(12) United States Patent
Janganati et al.

(10) Patent No.: US 10,428,082 B2
(45) Date of Patent: Oct. 1, 2019

(54) TRIAZOLE DERIVATIVES OF MELAMPOMAGNOLIDE B AND METHODS OF USE THEREOF

(71) Applicants: BioVentures, LLC, Little Rock, AR (US); The Regents of the University of Colorado, Denver, CO (US)

(72) Inventors: Venumadhav Janganati, Little Rock, AR (US); Peter Crooks, Little Rock, AR (US); Jessica Ponder, Denver, CO (US); Craig Jordan, Denver, CO (US)

(73) Assignees: BioVentures, LLC, Little Rock, AR (US); The Regents of the University of Colorado, A Body, Denver, CO (US)

( * ) Notice: Subject to any disclaimer, the term of this patent is extended or adjusted under 35 U.S.C. 154(b) by 0 days.

(21) Appl. No.: 16/073,705

(22) PCT Filed: Jan. 27, 2017

(86) PCT No.: PCT/US2017/015376
§ 371 (c)(1),
(2) Date: Jul. 27, 2018

(87) PCT Pub. No.: WO2017/132528
PCT Pub. Date: Aug. 3, 2017

(65) Prior Publication Data
US 2019/0040077 A1    Feb. 7, 2019

Related U.S. Application Data

(60) Provisional application No. 62/289,017, filed on Jan. 29, 2016.

(51) Int. Cl.
| | | |
|---|---|---|
| C07D 493/04 | (2006.01) |
| A61K 31/4192 | (2006.01) |
| A61P 35/00 | (2006.01) |
| C07C 57/15 | (2006.01) |

(52) U.S. Cl.
CPC ........ C07D 493/04 (2013.01); A61K 31/4192 (2013.01); A61P 35/00 (2018.01); C07C 57/15 (2013.01)

(58) Field of Classification Search
CPC .......................... C07D 493/04; A61K 31/4192
See application file for complete search history.

(56) References Cited

U.S. PATENT DOCUMENTS

| | | | |
|---|---|---|---|
| 4,241,046 A | 12/1980 | Papahadjopoulos |
| 4,394,448 A | 7/1983 | Szoka et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Mueller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,264,618 A | 11/1993 | Felgner et al. |
| 7,312,242 B2 | 12/2007 | Crooks et al. |
| 7,678,904 B2 | 3/2010 | Crooks et al. |
| 8,884,027 B2 | 11/2014 | Crooks et al. |
| 9,469,650 B2 | 10/2016 | Janganati et al. |
| 9,487,536 B2 | 11/2016 | Bommagani et al. |
| 9,908,892 B2 | 3/2018 | Janganati et al. |
| 9,920,063 B2 | 3/2018 | Bommagani et al. |
| 9,981,990 B2 * | 5/2018 | Janganati ............. C07F 7/1804 |
| 10,118,935 B2 | 11/2018 | Janganati et al. |
| 2007/0015161 A1 | 1/2007 | Echeverri et al. |
| 2007/0111203 A1 | 5/2007 | Cao et al. |
| 2009/0312298 A1 | 12/2009 | Bamber et al. |
| 2011/0092762 A1 | 4/2011 | Wong et al. |
| 2012/0122943 A1 | 5/2012 | Crooks et al. |
| 2014/0045821 A1 | 2/2014 | Wipf et al. |
| 2015/0133444 A1 | 5/2015 | Janganati et al. |
| 2015/0203508 A1 | 7/2015 | Bommagani et al. |
| 2016/0077084 A1 | 3/2016 | MacNicol et al. |
| 2016/0083397 A1 | 3/2016 | Penthala et al. |
| 2016/0368928 A1 | 12/2016 | Bommagani et al. |
| 2016/0368929 A1 | 12/2016 | Janganati et al. |
| 2017/0362254 A1 | 12/2017 | Janganati et al. |
| 2018/0237458 A1 | 8/2018 | Janganati et al. |

FOREIGN PATENT DOCUMENTS

| | | |
|---|---|---|
| EP | 2125859 B1 | 5/2013 |
| WO | 2008022104 A1 | 2/2008 |
| WO | 2012145678 A1 | 10/2012 |
| WO | 2013019561 A1 | 2/2013 |
| WO | 2014172607 A1 | 10/2014 |
| WO | 2014172608 A2 | 10/2014 |

(Continued)

OTHER PUBLICATIONS

Acton, E. et al., "Anticancer Specificity of Some Ellipticinium Salts against Human Brain Tumors in Vitro," J. Med. Chem., 1994, pp. 2185-2189, vol. 37.

Arumugam, K. et al., "Autoregulation of Musashi1 mRNA Translation During Xenopus Oocyte Maturation," NIH Public Access, Author Manuscript, available in PMC Dec. 2, 2013, pp. 1-23, published in final edited form as: Mol. Reprod. Dev., Aug. 2012, vol. 79, No. 8.

Bork, P. et al., "Sesquiterpene lactone containing Mexican Indian medicinal plants and pure sesquiterpene lactones as potent inhibitors of transcription factor NF-kB," FEBS Letters, 1997, pp. 85-90, vol. 402, Federation of European Biochemical Societies.

(Continued)

*Primary Examiner* — Golam M Shameem

(74) *Attorney, Agent, or Firm* — Polsinelli PC

(57) ABSTRACT

The present disclosure relates to triazole derivatives of melampomagnolide B, their synthesis, and their use as anti-cancer compounds.

5 Claims, 9 Drawing Sheets

(7 of 9 Drawing Sheet(s) Filed in Color)

(56) References Cited

FOREIGN PATENT DOCUMENTS

| WO | 2014197591 A2 | 12/2014 |
|---|---|---|
| WO | 2016090166 A1 | 6/2016 |
| WO | 2017132528 A1 | 8/2017 |

OTHER PUBLICATIONS

Boyd, M. et al., "Some Practical Considerations and Applications of the National Cancer Institute In Vitro Anticancer Drug Discovery Screen," Drug Development Research, 1995, 13 pgs., vol. 34.

Brouwers, L. et al., "Network Neighbors of Drug Targets Contribute to Drug Side-Effect Similarity," PloS ONE, Jul. 2011, pp. 1-7, vol. 6, Issue 7, No. 222187.

Cha, H. et al., "Evoluntionarily Repurposed Networks Reveal the Well-Known Antifungal Drug Thiabendazole to Be a Novel Vascular Disrupting Agent," PLOS Biol., Aug. 2012, pp. 1-13, vol. 10, No. 8, No. e1001379.

Cotarca, L. et al., "Bis(trichloromethyl) Carbonate in Organic Synthesis," Synthesis, Jan. 1, 1996, pp. 553-576, vol. 1996, No. 5, Georg Thieme Verlag KG.

Dai, Y. et al., "The NF (Nuclear factor)-kB inhibitor parthenolide interacts with histone deacetylase inhibitors to induce MKK7/JNK1-dependent apoptosis in human acute myeloid leukaemia cells," British Journal of Haematology, Aug. 4, 2010, pp. 70-83, vol. 151, Blackwell Publishing Ltd.

De Groot, F. et al., "Synthesis and Biological Evaluation of 2'-Carbamate-Linked and 2'-Carbonate-Linked Prodrugs of Paclitaxel: Selective Activation by the Tumor-Associated Protease Plasmin," J. Med. Chem., 2000, pp. 3093-3102, vol. 43.

Dell'Agli, M. et al., "Inhibition of NF-kB and metalloproteinase-9 expression and secretion by parthenolide derivatives," Bioorganic & Medicinal Chemistry Letters, 2009, pp. 1858-1860, vol. 19, Elsevier Ltd.

Deschler, B. et al., "Acute Myeloid Leukemia: Epidemiology and Etiology," Cancer, Nov. 1, 2006, pp. 2099-2107, vol. 107, No. 9, Wiley Interscience.

Deshpande, A. et al., "Insulin Induction of Xenopus laevis Oocyte Maturation Is Inhibited by Monoclonal Antibody against p21 ras Proteins," Mol. Cell. Biol., Mar. 1987, pp. 1285-1288, vol. 7, No. 3.

Deshpande, A. et al., "In vitro Induction of Germinal Vesicle Breakdown in Xenopus laevis Oocytes in Melittin," Differentiation, 1982, pp. 127-132, vol. 21, Springer-Verlag.

El-Feraly, F., "Melampolides From Magnolia Grandiflora," Phytochemistry, 1984, pp. 2372-2374, vol. 23, No. 10, Pergamon Press Ltd., Great Britain.

Estey, E. et al., "Acute myeloid leukaemia," Lancet, Nov. 25, 2006, pp. 1894-1907, vol. 368.

Ghantous, A. et al., "What made sesquiterpene lactones reach cancer clinical trials?", Drug Discovery Today, Aug. 2010, pp. 668-678, vol. 15, Nos. 15/16, Elsevier Ltd.

Gopal, Y.N. et al., "Parthenolide Specifically Depletes Histone Deacetylase 1 Protein and Induces Cell Death through Ataxia Telangiectasia Mutated," Chemistry & Biology, Jul. 2007, pp. 813-823, vol. 14, Elsevier Ltd.

Guo, Y., "The Role of Aven in Cell Cycle Regulation," Dissertation, Department of Pharmacology and Cancer Biology, Duke University, Aug. 13, 2008, pp. 1-147, (166 total pgs.), ProQuest, LLC.

Guzman, M. et al., "The sesquiterpene lactone parthenolide induces apoptosis of human acute myelogenous leukemia stem and progenitor cells," Blood, Jun. 1, 2005, pp. 4163-4169, vol. 105, No. 11.

Guzman, M. et al., "Feverfew: weeding out the root of leukaemia," Expert Opin. Biol. Ther., 2005, pp. 1147-1152, vol. 5, No. 9, Ashley Publications Ltd.

Guzman, M. et al., "An orally bioavailable pathenolide analog selectively eradicates acute myelogenous leukemia stem and progenitor cells," Blood, Dec. 15, 2007, pp. 4427-4435, vol. 110, No. 13.

Hall, I. et al., "Anti-Inflammatory Activity of Sesquiterpene Lactones and Related Compounds," J. Pharmaceutical Sciences, May 1979, pp. 537-542, vol. 68, No. 5.

Han, C. et al., "Semisynthetic Derivatives of Sesquiterpene Lactones by Palladium-Catalyzed Arylation of the alpha-Methylene-gamma-lactone Substructure," J. Org. Chem., 2009, pp. 7176-7179, vol. 74.

Hassane, D. et al., "Chemical genomic screening reveals synergism between parthenolide and inhibitors of the PI-3 kinase and mTOR pathways," Blood, Dec. 23, 2010, pp. 5983-5990, vol. 116, No. 26.

Hehner, S. et al., "Sesquiterpene Lactones Specifically Inhibit Activation of NF-kB by Preventing the Degradation of IkB-alpha and IkB-beta," J. Biol. Chem., 1998, pp. 1288-1297, vol. 273, No. 3.

Heptinstall, S. et al., "Inhibition of Platelet Behaviour by Feverfew: a Mechanism of Action Involving Sulphydryl Groups," Folia Haematol., 1988, pp. 447-449, vol. 115, No. 4.

Hewamana, S. et al., "The NF-kB subunit Rel A is associated with in vitro survival and clinical disease progression in chronic lymphocytic leukemia and represents a promising therapeutic target," Blood, May 1, 2008, pp. 4681-4689, vol. 111, No. 9.

International Search Report and Written Opinion dated Feb. 5, 2016 from related International Patent Application No. PCT/US2015/063792; 10 pgs.

International Search Report and Written Opinion dated Nov. 7, 2014 from related International Patent Application No. PCT/US2014/034605; 11 pgs.

International Search Report and Written Opinion dated Sep. 12, 2014 from related International Patent Application No. PCT/US2014/034604; 9 pgs.

International Search Report and Written Opinion dated Apr. 25, 2017 from related International Patent Application No. PCT/US2017/015376; 13 pgs.

Janganati, V. et al., "Anti-cancer activity of carbamate derivatives of melampomagnolide B," Bioorg. Med. Chem. Lett., 2014, pp. 3499-3502, vol. 24, Elsevier Ltd.

Janganati, V. et al., "MMB triazole analogs are potent NF-kB inhibitors and anti-cancer agents against both hematological or cells," Euro. J. Med. Chem., 2018, pp. 562-581, vol. 157, Elsevier Masson SAS.

Kim, Y. et al., "Resistance of cholangiocarcinoma cells to parthenolide-induced apoptosis by the excretory-secretory products of Clonorchis sinensis," Parasitol. Res., 2009, pp. 1011-1016, vol. 104, Springer.

Kim, Y. et al., "Myeloperoxidase Expression as a Potential Determinant of Parthenolide-Induced Apoptosis in Leukemia Bulk and Leukemia Stem Cells," JPET, 2010, pp. 389-400, vol. 335, No. 2.

Knight, D., "Feverfew: Chemistry and Biological Activity," Natural Products Reports, 1995, pp. 271-276.

Kodadek, T. et al., "Optimized protocols for the isolation of specific protein-binding peptides or peptoids from combinatorial libraries displayed on beads," Mol. BioSyst., 2006, pp. 25-35, vol. 2, The Royal Society of Chemistry.

Kolev, J. et al., "Discovery of potent parthenolide-based antileukemic agents enabled by late-stage P450-mediated C—H functionalization," NIH Public Access, Author Manuscript, 2015, pp. 1-22, published in final edited form as: ACS Chem. Biol., Jan. 17, 2014, pp. 164-173, vol. 9, No. 1.

Lowenberg, B. et al., "Mitoxantrone Versus Daunorubicin in Induction-Consolidation Chemotherapy—The Value of Low-Dose Cytarabine for Maintenance of Remission, and an Assessment of Prognostic Factors in Acute Myeloid Leukemia in the Elderly: Final Report of the Leukemia Cooperative Group of the European Organization for the Research and Treatment of Cancer and the Dutch-Belgian Hemato-Oncology Cooperative Hovon Group Randomized Phase III Study AML-9," J. Clin. Oncol., 1998, pp. 872-881, vol. 16, No. 3.

Macias, F. et al., "Potential Allelopathic Activity of Several Sesquiterpene Lactone Models," Phytochemistry, 1992, pp. 1969-1977, vol. 31, No. 6, Pergamon Press Ltd., Great Britain.

Mood, K. et al., "Contribution of JNK, Mek, Mos and PI-3K signaling to GVBD in Xenopus oocytes," Cellular Signalling, 2004, pp. 631-642, vol. 16, Elsevier Inc.

(56) References Cited

OTHER PUBLICATIONS

Moumou, M. et al., "Access to new sequiterpenoids by catalytic acid rearrangement of 9alpha-hydroxyparthenolide," Tetrahedron Lett., 2012, pp. 3000-3003, vol. 53, Elsevier Ltd.
Nasim, S. et al., "Antileukemic activity of aminoparthenolide analogs," Bioorg. Med. Chem. Lett., 2008, pp. 3870-3873, vol. 18, Elsevier Ltd.
Nasim, S. et al., "Melampomagnolide B: A new antileukemic sesquiterpene," Bioorg. Med. Chem., 2011, pp. 1515-1519, vol. 19, Elsevier Ltd.
Neelakantan, S. et al., "Aminoparthenolides as novel anti-leukemic agents: Discovery of the NF-kB inhibitor, DMAPT (LC-1)," Bioorg. Med. Chem. Lett., 2009, pp. 4346-4349, vol. 19, Elsevier Ltd.
Neukirch, H. et al., "Transannular Cyclization in Cyclodecenes: The Case Study of Melampolides," Eur. J. Org. Chem., 2003, pp. 3969-3975, Wiley-VCH Verlag GmbH & Co. KGaA, Weinheim.
Notice of Allowance dated Jun. 7, 2016 from related U.S. Appl. No. 14/537,389; 9 pgs.
Notice of Allowance dated Jun. 8, 2016 from related U.S. Appl. No. 14/676,537; 8 pgs.
Notice of Allowance dated Dec. 27, 2017 from related U.S. Appl. No. 15/254,849; 7 pgs.
Notice of Allowance dated Jan. 18, 2018 from related U.S. Appl. No. 15/251,889; 6 pgs.
Notice of Allowance dated Jan. 19, 2018 from related U.S. Appl. No. 15/532,413; 7 pgs.
Notice of Allowance dated Jun. 15, 2018 from related U.S. Appl. No. 15/957,524; 5 pgs.
Nozaki, S. et al., "Repression of GADD153/CHOP by NF-kB: a possible cellular defense against endoplasmic reticulum stress-induced cell death," Oncogene, 2001, pp. 2178-2185, vol. 20, Nature Publishing Group.
Office Action dated Oct. 5, 2015 from related U.S. Appl. No. 14/537,389; 10 pgs.
Office Action dated Mar. 11, 2016 from related U.S. Appl. No. 14/537,389; 8 pgs.
Office Action dated Feb. 8, 2016 from related U.S. Appl. No. 14/676,537; 19 pgs.
Office Action dated Jul. 29, 2016 from related U.S. Appl. No. 14/785,196; 12 pgs.
Office Action dated Jan. 25, 2017 from related U.S. Appl. No. 14/785,196; 20 pgs.
Office Action dated Jun. 1, 2017 from related U.S. Appl. No. 14/785,196; 17 pgs.
Office Action dated Jun. 9, 2016 from related U.S. Appl. No. 14/785,183; 18 pgs.
Office Action dated Feb. 13, 2017 from related U.S. Appl. No. 14/785,183; 12 pgs.
Office Action dated Aug. 9, 2017 from related U.S. Appl. No. 15/251,889; 16 pgs.
Office Action dated Aug. 9, 2017 from related U.S. Appl. No. 15/254,849; 16 pgs.
Office Action dated Oct. 18, 2017 from related U.S. Appl. No. 14/785,196; 16 pgs.
Office Action dated Mar. 7, 2018 from related U.S. Appl. No. 14/785,196; 20 pgs.
Oka, D. et al., "Sesquiterpene lactone parthenolide suppresses tumor growth in a xenograft model of renal cell carcinoma by inhibiting the activation of NF-kB," Int. J. Cancer, 2007, pp. 2576-2581, vol. 120, Wiley-Liss, Inc.
Okada, I. et al., "Stabilization of Actin Filaments Prevents Germinal Vesicle Breakdown and Affects Microtubule Organization in Xenopus Oocytes," Cytoskeleton, May 2012, pp. 312-323, vol. 69, Wiley Periodicals, Inc.
OncoLink, "Cancer Types," http://www.oncolink.org/cancers, 2017, pp. 1-17, Trustees of the University of Pennsylvania.
Papke, R. et al., "The pharmacological activity of nicotine and nornicotine on nAChRs subtypes: relevance to nicotine dependence and drug discovery," J. Neurochem., 2007, pp. 160-167, vol. 101.

Pei, S. et al., "Targeting Aberrant Glutathione Metabolism to Eradicate Human Acute Myelogenous Leukemia Cells," J. Biol. Chem., Nov. 22, 2013, pp. 33542-33558, vol. 288, No. 47.
Penthala, N. et al., "Heck products of parthenolide and melampomagnolide-B as anticancer modulators that modify cell cycle progression," European Journal of Medicinal Chemistry, 2014, pp. 517-525, vol. 85, Elsevier Masson SAS.
Pfaffenrath, V. et al., "The efficacy and safety of Tanacetum parthenium (feverfew) in migraine prophylaxis—a double-blind, multicentre, randomized placebo-controlled dose-response study," Cephalalgia, 2002, pp. 523-532, vol. 22, Blackwell Science Ltd., London.
Pubchem, Compound Summary for CID 44255396, Nov. 16, 2009; 3 pgs.
Ralstin, M. et al., "Parthenolide Cooperates with NS398 to Inhibit Growth of Human Hepatocellular Carcinoma Cells through Effects on Apoptosis and G0-G1 Cell Cycle Arrest," Mol. Cancer Res., Jun. 2006, pp. 387-399, vol. 4, No. 6.
Restriction Requirement with Notice of References Cited dated Oct. 6, 2015 from related U.S. Appl. No. 14/676,537; 11 pgs.
Riganti, C. et al., "Artemisinin induces doxorubicin resistance in human colon cancer cells via calcium-dependent activation of HIF-1alpha and P-glycoprotein overexpression," British Journal of Pharmacology, 2009, pp. 1054-1066, vol. 156.
Saadane, A. et al., "Parthenolide inhibits ERK and AP-1 which are dysregulated and contribute to excessive IL-8 expression and secretion in cystic fibrosis cells," J. Inflammation, 2011, pp. 1-15, vol. 8, No. 26, BioMed Central.
Sharma, G. et al., "Synthesis and Structure of alpha/delta-Hybrid Peptides—Access to Novel Helix Patterns in Foldamers," Chem. Eur. J., 2009, pp. 5552-5566, vol. 15, Wiley-VCH Verlag GmbH & Co. KgaA, Weinheim.
Sharma, G. et al., "Theoretical and Experimental Studies on alpha/E-Hybrid Peptides: Design of a 14/12-Helix from Peptides with Alternating (S)-C-Linked Carbo-E-amino Acid [(S)-E-Caa(x)] and L-Ala," J. Org. Chem., 2009, pp. 6703-6713, vol. 74, No. 17.
Skalska, J. et al., "Modulation of Cell Surface Protein Free Thiols: A Potential Novel Mechanism of Action of the Sesquiterpene Lactone Parthenolide," PLoS ONE, Dec. 2009, pp. 1-8, vol. 4, Issue 12, No. e8115.
Staab, H., "New Methods of Preparative Organic Chemistry IV. Syntheses Using Heterocyclic Amides (Azolides)," Angew. Chem. Internat. Edit, 1962, pp. 351-367, vol. 1, No. 7.
Stebbins-Boaz, B. et al., "CPEB controls the cytoplasmic polyadenylation of cyclin, Cdk2 and c-mos mRNAs and is necessary for oocyte maturation in Xenopus," EMBO J., May 1996, pp. 2582-2592, vol. 15, No. 10.
Sugimoto, H. et al., "Activation of Dithiocarbamate by 2-Halothiazolium Salts," J. Org. Chem., 1988, pp. 2263-2267, vol. 53, No. 10.
Sweeney, C. et al., "Nuclear Factor-kB Is Constitutively Activated in Prostate Cancer In vitro and Is Overexpressed in Prostatic Intraepithelial Neoplasia and Adenocarcinoma of the Prostate," Clin. Cancer Res., Aug. 15, 2004, pp. 5501-5507, vol. 10.
Tazzari, P. et al., "Multidrug resistance-associated protein 1 expression is under the control of the phosphoinositide 3 kinase/Akt signal transduction network in human acute myelogenous leukemia blasts," Leukemia, 2007, pp. 427-438, vol. 21, Nature Publishing Group.
Wen, J. et al., "Oxidative Stress-mediated Apoptosis. The Anticancer Effect of the Sesquiterpene Lactone Parthenolide," J. Biol. Chem., 2002, pp. 38954-38964, vol. 277, No. 41.
Wheeler, G. et al., "Xenopus: An Ideal System for Chemical Genetics," Genesis, 2012, pp. 207-218, vol. 50, Wiley Periodicals, Inc.
Won, Y-K. et al., "Parthenolide sensitizes ultraviolet (UV)-B-induced apoptosis via protein kinase C-dependent pathways," Carcinogenesis, 2005, pp. 2149-2156, vol. 26, No. 12, Oxford University Press.
Woods, J. et al., "Fluorinated Amino-Derivatives of the Sesquiterpene Lactone, Parthenolide, as 19F NMR Probes in Deuterium-Free Environments," J. Med. Chem., 2011, pp. 7934-7941, vol. 54, ACS Publications.

(56) References Cited

OTHER PUBLICATIONS

Yip-Schneider, M. et al., "Parthenolide and sulindac cooperate to mediate growth suppression and inhibit the nuclear factor-kB pathway in pancreatic carcinoma cells," Mol. Cancer Ther., Apr. 2005, pp. 587-594, vol. 4, No. 4.

Zhai, J.et al., "Biomimetic Semisynthesis of Arglabin from Parthenolide," J. Org. Chem., 2012, pp. 7103-7107, vol. 77, American Chemical Society.

Zhang, Q. et al., "Guaianolide Sesquiterpene Lactones, a Source To Discover Agents That Selectively Inhibit Acute Myelogenous Leukemia Stem and Progenitor Cells," J. Med. Chem., 2012, pp. 8757-8769, vol. 55, American Chemical Society.

Zhu, T. et al., "Differential Recognition of ACE Inhibitors in Xenopus Laevis Oocytes Expressing Rat PEPT1 and PEPT2," Pharmaceutical Res., 2000, pp. 526-532, vol. 17, No. 5, Plenum Publishing Corporation.

Extended European Search Report dated May 17, 2019 from related European Patent Application No. 17744985.7; 6 pages.

\* cited by examiner

TRIAZOLE DERIVATIVES OF MELAMPOMAGNOLIDE B AND METHODS OF USE THEREOF

CROSS REFERENCE TO RELATED APPLICATIONS

This application claims the benefit of International Application No. PCT/US2017/015376, filed Jan. 27, 2017 and U.S. Provisional Application No. 62/289,017, filed Jan. 29, 2016, the disclosures of which are hereby incorporated by reference in their entirety.

GOVERNMENTAL RIGHTS

This invention was made with government support under R01CA158275 awarded by the National Institutes of Health. The government has certain rights in the invention.

FIELD OF THE INVENTION

The present disclosure relates to triazole derivatives of melampomagnolide B, their synthesis, and their use as anti-cancer compounds.

BACKGROUND OF THE INVENTION

Parthenolide (PTL), an abundant sesquiterpene lactone found in the medicinal herb feverfew (*Tanacetum parthenium*), has undergone intense pharmacological research, especially for its antileukemic properties. Initial biomechanistic studies of PTL and its derivatives indicate that the compound promotes apoptosis by inhibiting the NF-kB transcription factor complex, thereby downregulating anti-apoptotic genes under NF-kB control. PTL and its derivatives may also interfere with glutathione function, specifically glutathione's ability to sequester reactive oxygen species. In culture, PTL induces robust apoptosis of primary acute myeloid leukemia (AML) cells in culture. To overcome poor water-solubility, PTL may be derivatized with an alkylamino, which can convert into water-soluble salts. A series of fluorinated amino derivatives of PTL exhibit activity in antiproliferative assays in HL-60 (human promyelocytic leukemia) cells. PTL has also been the source of several antileukemic compounds arising from chemical modification of the PTL molecule.

Melampomagnolide B (MMB), a melampolide originally isolated from *Magnolia grandiflora*, is an antileukemic sesquiterpene with properties similar to those of PTL. However, novel compounds with improved bioavailability and longer in vivo half-life and with increased water solubility are needed.

SUMMARY OF THE INVENTION

In an aspect, the disclosure provides a compound of Formula (I):

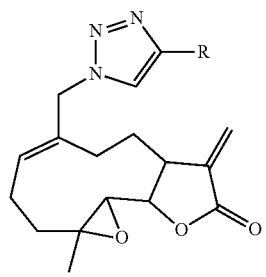

(I)

wherein:
R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, halogen, cyano, nitro, amidine, amino, carboxyl, ester, alkylalkylamino, dialkylamino, hydroxyl, alkoxy or arylalkoxy (e.g. methoxy, ethoxy, benzyloxy, substituted benzyloxy) and combinations thereof.

In another aspect, the disclosure provides a compound of Formula (II):

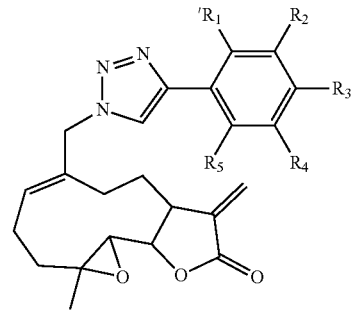

(II)

wherein:
$R_1$, $R_2$, $R_3$, $R_4$, and $R_5$ are each independently selected from the group consisting of hydrogen, hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, halogen, cyano, nitro, amidine, amino, carboxyl, ester, alkylalkylamino, dialkylamino, hydroxyl, alkoxy or arylalkoxy (e.g. methoxy, ethoxy, benzyloxy, substituted benzyloxy) and combinations thereof; and $R_1$ and $R_2$ or $R_2$ and $R_3$ or $R_3$ and $R_4$ or $R_4$ and $R_5$ together can optionally form an optionally substituted cycloalkyl, aryl or heteroaryl 5 or 6 membered ring.

In still another aspect, the disclosure provides a method of making the compound comprising Formula (I) or (II), the method comprising contacting an azido derivative of melampomagnolide B with an acetylenic compound in the presence of copper catalyst, a proton acceptor and a solvent to afford a compound of Formula (I) or (II).

In still yet another aspect, the disclosure provides a method of making the compound comprising Formula (I) or (II), the method comprising: (a) contacting MMB mesylate with alkyl azide in the presence of a solvent to afford an azido derivative of MMB; and (b) contacting the azido derivative of melampomagnolide B with an acetylenic compound in the presence of copper catalyst, a proton acceptor and a solvent to afford a compound of Formula (I) or (II).

In a different aspect, the disclosure provides a method of making the compound comprising Formula (I) or (II), the method comprising: (a) contacting MMB with a mesylate in the presence of a proton acceptor and a solvent to afford MMB mesylate; (b) contacting the MMB mesylate with alkyl azide in the presence of a solvent to afford an azido derivative of MMB; and (c) contacting the azido derivative of melampomagnolide B with an acetylenic compound in the presence of copper catalyst, a proton acceptor and a solvent to afford a compound of Formula (I) or (II).

In other aspects, the disclosure provides a method to induce HO-1 expression, the method comprising contacting a cell with a composition comprising a compound of Formula (I) or (II). Additionally, the disclosure provides a method to inhibit the NF-κB pathway, the method comprising contacting a cell with a composition comprising a compound of Formula (I) or (II). Further, the disclosure provides a method for inhibiting growth of a cancer cell in a subject, the method comprising administering to the subject a composition comprising a compound of Formula (I) or (II). Still further, the disclosure provides a method of treating, stabilizing or preventing cancer, the method comprising administering to a subject a composition comprising a compound of Formula (I) or (II).

BRIEF DESCRIPTION OF THE DRAWINGS

The application file contains at least one photograph executed in color. Copies of this patent application publication with color photographs will be provided by the Office upon request and payment of the necessary fee.

FIG. 3A is AML1; FIG. 3B and FIG. 3C are AML2; and FIG. 3D is AML3.

DETAILED DESCRIPTION OF THE INVENTION

Figure 1A:
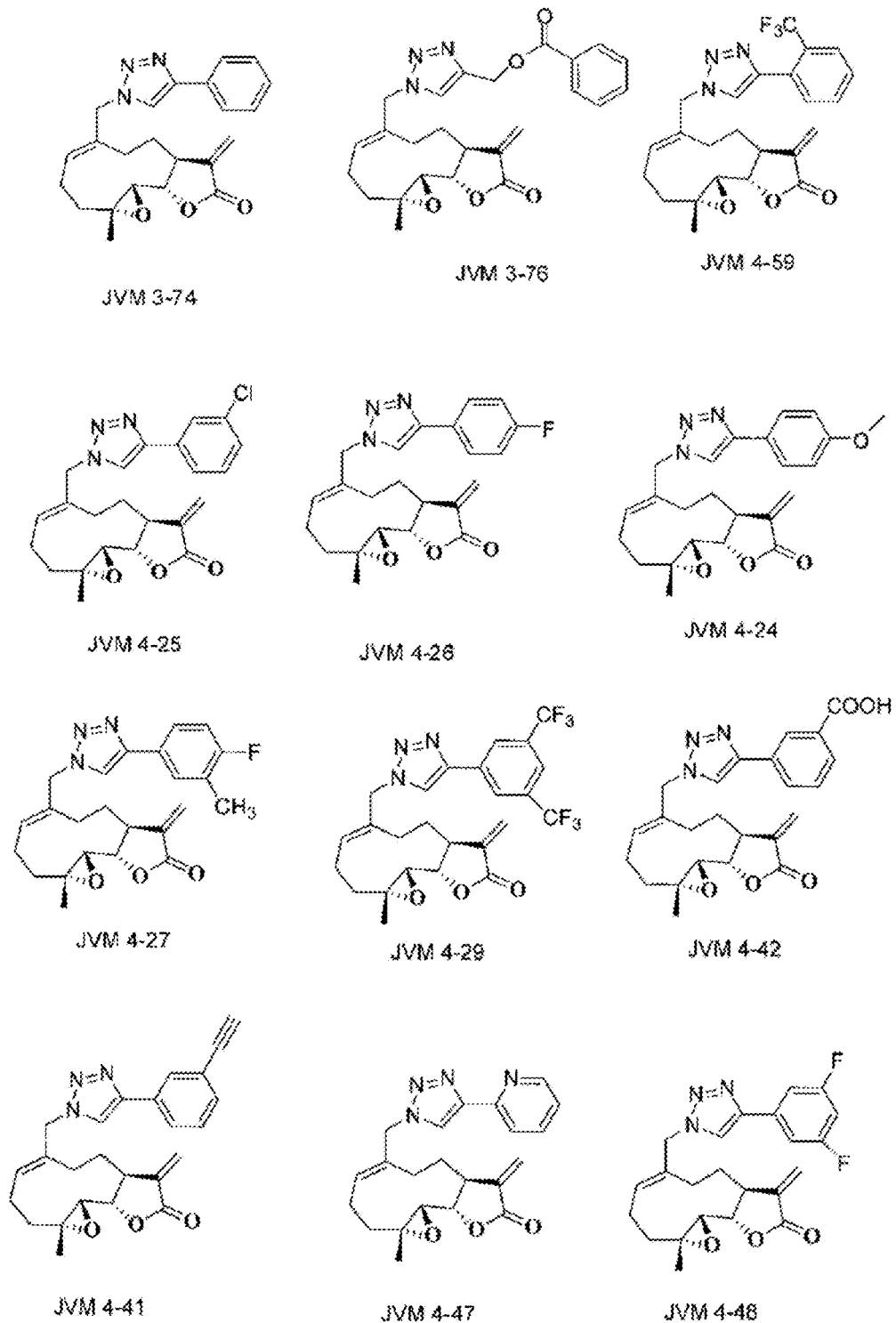
FIG. 1A and FIG. 1B depict structures of triazole derivatives of melampomagnolide B.

MMB can be synthesized from parthenolide via selenium oxide oxidation of the C10 methyl group of PTL, which also results in concomitant conversion of the geometry of the C9-C10 bond from trans to cis. The structure of the MMB molecule provides more scope and opportunities for the synthesis of various derivatives of MMB than PTL, since the MMB molecule contains an allylic hydroxyl group at C-14, which allows the synthesis of a wide variety of new MMB derivatives via conjugation chemistry. To further enhance anti-cancer activity and improve the drug-like properties of sesquiterpenes, a library of triazole derivatives of melampomagnolide B were designed and synthesized by utilizing azido derivatives of melampomagnolide B and acetylenic reagents via click chemistry methodologies. The synthetic procedures and anti-cancer activities of these novel analogs are described in the current disclosure. The compounds showed excellent anti-leukemic activity in the nanomolar concentration range.

I. Composition (a) Compound Comprising Formula (I) and (II)

One aspect of the invention provides compounds comprising Formula (I):

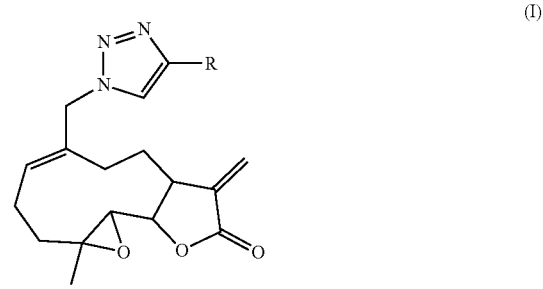

wherein:
R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, halogen, cyano, nitro, amidine, amino, carboxyl, ester, alkylalkylamino, dialkylamino, hydroxyl, alkoxy or arylalkoxy (e.g. methoxy, ethoxy, benzyloxy, substituted benzyloxy) and combinations thereof.

In one embodiment, a compound comprises Formula (I), wherein R is selected from the group consisting of a simple or substituted phenyl, a simple or substituted biphenyl ring system, a simple or substituted carbocyclic ring system such as cycloalkane, cycloalkane, or a combination thereof, a simple or substituted heterocyclic ring system such as azitidine, pyridine, pyrrole, pyrrolidine, pyran, piperidine, imidazole, thiazole, dioxane, morpholine, pyrimidine, pyrazole, isoxazole, oxazole, isothiazole, thiazole, thiadiazine, dithiazine, 1,4-thiazepine, thiophene, furan, indole, isoindole, indolizine, benzofuran, benzothiophene, benzothiazole, quinoline, isoquinoline, purine, carbazole, dibenzofuran, chromene, coumarin, xanthene, quinazoline or quinoxaline.

In another embodiment, a compound comprises Formula (I), wherein R is selected from the group consisting of a simple or substituted phenyl, a simple or substituted heterocycle, and a simple or substituted alkyl.

In still another embodiment, a compound comprises Formula (I), wherein R is selected from the group consisting of:

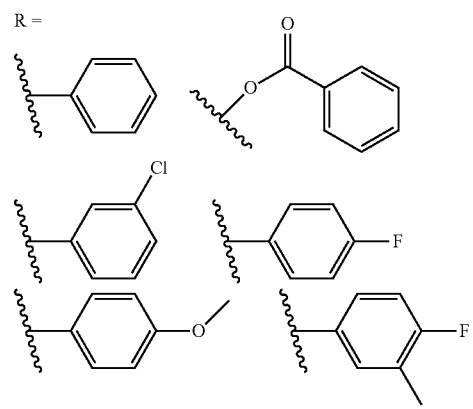

-continued

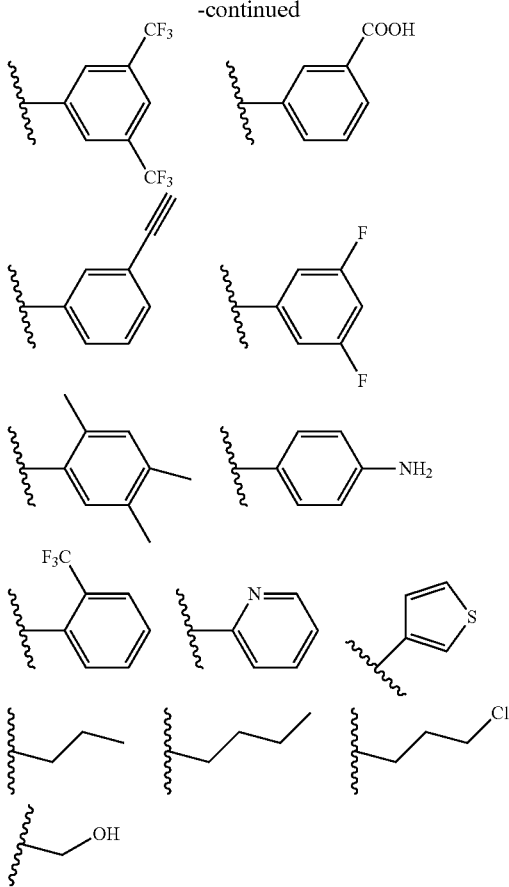

Another aspect of the invention provides compounds comprising Formula (II):

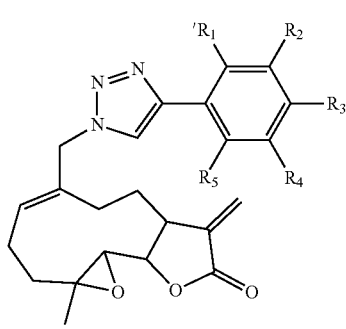

wherein:
R₁, R₂, R₃, R₄, and R₅ are each independently selected from the group consisting of hydrogen, hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, halogen, cyano, nitro, amidine, amino, carboxyl, ester, alkylalkylamino, dialkylamino, hydroxyl, alkoxy or arylalkoxy (e.g. methoxy, ethoxy, benzyloxy, substituted benzyloxy) and combinations thereof; and R₁ and R₂ or R₂ and R₃ or R₃ and R₄ or R₄ and R₅ together can optionally form an optionally substituted cycloalkyl, aryl or heteroaryl 5 or 6 membered ring.

In one embodiment, a compound comprises Formula (II), wherein R₁, R₂, R₃, R₄, and R₅ are each independently selected from the group consisting of hydrogen, alkyl, substituted alkyl, alkynyl, methyl, trifluoromethyl, halogen, cyano, nitro, amidine, amino, carboxyl, ester, alkylalkylamino, dialkylamino, hydroxyl, alkoxy or arylalkoxy (e.g. methoxy, ethoxy, benzyloxy, substituted benzyloxy) and combinations thereof.

In another embodiment, a compound comprises Formula (II), wherein R₁, R₂, R₃, R₄, and R₅ are each independently selected from the group consisting of hydrogen, alkynyl, methyl, trifluoromethyl, halogen, amino, carboxyl, ester, hydroxyl, alkoxy (e.g. methoxy, ethoxy) and combinations thereof.

Alkylalkylamino groups are disubstituted amine groups. Each of the alkyl groups may be the same or different. In one embodiment, both alkyl groups are lower alkyl groups. The amidine nitrogen groups may be further substituted by hydrogen, alkyl, or substituted alkyl at each position. Preferably, the amidine nitrogens are each substituted by hydrogen. Where the group is an amine, the amine may be a primary, secondary, or tertiary amine. Preferably, amine substituents are lower alkyl groups. Ester groups may be attached at either the carbonyl end or at the oxygen end of the ester. The opposite terminus of the ester may be alkyl or substituted alkyl. Preferably, the ester is a lower alkyl.

The compound comprising Formula (I) or (II) may be a free form or a salt. When the compound is in a salt form, the salt is preferably a pharmaceutically acceptable salt. Pharmaceutically acceptable salts may include, without limitation, hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpropionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like. In other embodiments, the pharmaceutically acceptable salt includes an alkaline or alkaline earth metal ion salt. In particular, sodium, potassium or other pharmaceutically acceptable inorganic salts are used. The salt forms may be amorphous or in various polymeric forms including hydrates, or solvates with alcohols or other solvents. In a specific embodiment, Formula (I) or (II) may be a fumarate salt. Specifically, a dimethylamino adduct as a fumarate salt may be prepared by reaction of a compound of Formula (I) or (II) with dimethylamine in methanol followed by conversion to the corresponding fumarate salt, which is more water soluble than the free base form.

(b) Pharmaceutical Compositions

The disclosure also provides a pharmaceutical composition comprising the compound comprising Formula (I) or (II) and at least one pharmaceutically acceptable excipient. In various embodiments, one or more of the compounds described in Section 1(a) may be combined with at least one pharmaceutically acceptable excipient.

(i) Excipient

A pharmaceutical composition of the disclosure comprises at least one pharmaceutically acceptable excipient. Non-limiting examples of suitable excipients may include diluents, binders, fillers, buffering agents, pH modifying agents, disintegrants, dispersing agents, stabilizers, preservatives, and coloring agents. The amount and types of excipients may be selected according to known principles of pharmaceutical science.

In one embodiment, the excipient may include at least one diluent. Non-limiting examples of suitable diluents may include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose.

In another embodiment, the excipient may comprise a binder. Suitable binders may include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers may include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Buffers may include phosphates, carbonates, citrates, and the like. Representative examples of suitable buffering agents may include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be sodium carbonate or sodium bicarbonate.

In another alternate embodiment, the excipient may also include a preservative. Non-limiting examples of suitable preservatives may include antioxidants, such as alpha-tocopherol or ascorbate, or EDTA (ethylenediaminetetraacetic acid), EGTA (ethylene glycol tetraacetic acid), BHA (butylated hydroxyanisole), BHT (butylated hydroxytoluene), and the like.

In a further embodiment, the excipient may include a disintegrant. Suitable disintegrants may include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In a further embodiment, the excipient may include a lubricant. Non-limiting examples of suitable lubricants may include minerals such as talc or silica; and fats such as vegetable stearin, magnesium stearate, or stearic acid.

In still another embodiment, it may be desirable to provide a coloring agent. Suitable color additives may include, but are not limited to, food, drug and cosmetic colors (FD&C), drug and cosmetic colors (D&C), or external drug and cosmetic colors (Ext. D&C).

The weight fraction of the excipient(s) in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The pharmaceutical composition may be mixed with one or more excipients to form a solid, liquid, or cream dosage form. Methods of formulating a solid, liquid, or cream dosage form are known in the art.

(ii) Optional Additional Pharmaceutical Ingredient

Optionally, the compound comprising Formula (I) or (II) may be combined with other compounds comprising Formula (I) or (II) may be combined with one or more than one additional active pharmaceutical ingredients.

II. Method for Synthesis (a) Method for Producing a Compound Comprising Formula (I) or (II)

The present disclosure also describes the synthesis of various triazole derivatives of melampomagnolide B by reaction of an azido derivative of melampomagnolide B with a variety of acetylenic reagents in presence of copper catalyst, triethylamine and acetonitrile-water utilizing click chemistry methodologies. To afford the azido derivative, MMB mesylate was reacted with sodium azide in the presence of dimethylformamide and acetonitrile at 80° C. for 1 h.

In one embodiment, the disclosure provides a method of making the compound comprising Formula (I) or (II). The method comprises contacting an azido derivative of melampomagnolide B with an acetylenic compound in the presence of copper catalyst, a proton acceptor and a solvent to afford a compound of Formula (I) or (II).

In another embodiment, the method comprises: (a) contacting MMB mesylate with alkyl azide in the presence of a solvent to afford an azido derivative of MMB; and (b) contacting the azido derivative of melampomagnolide B with an acetylenic compound in the presence of copper catalyst, a proton acceptor and a solvent to afford a compound of Formula (I) or (II).

In still another embodiment, the method comprises: (a) contacting MMB with a mesylate in the presence of a proton acceptor and a solvent to afford MMB mesylate; (b) contacting the MMB mesylate with alkyl azide in the presence of a solvent to afford an azido derivative of MMB; and (c) contacting the azido derivative of melampomagnolide B with an acetylenic compound in the presence of copper catalyst, a proton acceptor and a solvent to afford a compound of Formula (I) or (II).

(a) MMB to MMB Mesylate

In an aspect, the method may comprise, in part, contacting MMB with a mesylate in the presence of triethylamine and a solvent to afford MMB mesylate.

A mesylate is any salt or ester of methanesulfonic acid ($CH_3SO_3H$). In salts, the mesylate is present as the $CH_3SO_3^-$ anion. In a specific embodiment, the mesylate is mesylate chloride.

The mole to mole ratio of MMB to the mesylate can range over different embodiments of the invention. In one embodiment, the ratio of MMB to the mesylate varies from about 0.1:1 to about 1:10. In some embodiments, the mole to mole ratio of MMB to the mesylate is about 0.5:1 to about 1:5. In various embodiments, the mole to mole ratio of MMB to the mesylate is about 0.6:1, about 0.7:1, about 0.8:1, about 0.9:1, about 1:1, about 1:1.1, about 1:1.2, about 1:1.3, about 1:1.4, or about 1:1.5. In an exemplary embodiment, the mole to mole ratio of MMB to the mesylate is 1:1.

The reaction is preferably carried out in a solvent and is more preferably carried out in an organic solvent. The solvent may be chosen without limitation from including alkane and substituted alkane solvents (including cycloalkanes) alcohol solvents, halogenated solvents, aromatic hydrocarbons, esters, ethers, ketones, and combinations thereof. Non-limiting examples of suitable organic solvents are acetonitrile, acetone, allyl alcohol, benzene, butyl acetate, chlorobenzene, chloroform, chloromethane, cyclohexane, cyclopentane, dichloromethane (DCM), dichloroethane, diethyl ether, dimethoxyethane (DME), dimethylformamide (DMF), dimethyl sulfoxide (DMSO), dioxane, ethanol, ethyl acetate, ethylene dichloride, ethylene bromide, formic acid, fluorobenzene, heptane, hexane, isobutylmethylketone, isopropanol, isopropyl acetate, N-methylpyrrolidone, methanol, methylene bromide, methylene chloride, methyl iodide, methylethylketone, methyltetrahydrofuran, pentyl acetate, propanol, n-propyl acetate, sulfolane, tetrahydrofuran (THF), tetrachloroethane, toluene, trichloroethane, water, xylene and combinations thereof. In an embodiment, a solvent may be a non-polar solvent. Non-limiting examples of non-polar solvents include pentane, cyclopentane, hexane, cyclohexane, benzene, toluene, xylene, 1,4-dioxane, chloroform, diethyl ether and dichloromethane. In an exemplary embodiment, a solvent is dichloromethane.

A proton acceptor is generally added to facilitate the reaction. The proton acceptor generally has a pKa greater than about 7, or from about 7 to about 13, or more preferably from about 8 to about 10. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In an exemplary embodiment, the proton acceptor is triethylamine.

The amount of time over which the reaction is conducted may also vary within different embodiments. In some embodiments, the reaction may be conducted over a period of about 10 minutes to about 12 hours. In particular embodiments, the reaction is carried out for about 10 minutes, about 20 minutes, about 30 minutes, about 40 minutes, about 50 minutes, about 60 minutes, about 2 hours, about 3 hours, about 4 hours, about 5 hours, about 6 hours, about 7 hours, about 8 hours, about 9 hours, about 10 hours, about 11 hours, or about 12 hours. In an exemplary embodiment, the reaction is conducted for about 30 minutes.

The temperature may vary over different embodiments, in some embodiments the temperature may range from about 0° C. to about 40° C. In particular embodiments the temperature may range from about 0° C. to about 35° C., from about 0° C. to about 25° C., from about 0° C. to about 15° C., or from about 0° C. to about 5° C. In an exemplary embodiment, the reaction is conducted at about 0° C.

The synthesized compounds may be used in their crude form or they may be purified. The compounds may be purified by any suitable method known in the art including through column chromatography, crystallization, distillation, extraction, and the like. In one specific embodiment, the compounds are washed with water, extracted with dichloromethane, and concentrated.

(b) MMB Mesylate to Azido Derivative of MMB

In another aspect, the method may comprise, in part, contacting a MMB mesylate with alkyl azide in the presence of a solvent to afford an azido derivative of MMB.

An azide is an anion with the formula $N_3^-$. An alkyl azide is selected from the group consisting of sodium azide, potassium azide and trimethyl silyl azide. In a specific embodiment, the alkyl azide is sodium azide.

The mole to mole ratio of MMB mesylate to the alkyl azide can range over different embodiments of the invention. In one embodiment, the ratio of MMB mesylate to the alkyl azide varies from about 0.1:1 to about 1:10. In some embodiments, the mole to mole ratio of MMB mesylate to the alkyl azide is about 1:1 to about 1:5. In various embodiments, the mole to mole ratio of MMB mesylate to the alkyl azide is about 1:1.5, about 1:1.6, about 1:1.7, about 1:1.8, about 1:1.9, about 1:2, about 1:2.1, about 1:2.2, about 1:2.3, about 1:2.4, or about 1:2.5. In an exemplary embodiment, the mole to mole ratio of MMB mesylate to the alkyl azide is 1:2.

The reaction is preferably carried out in a solvent and is more preferably carried out in an organic solvent. The solvent may be chosen without limitation from including alkane and substituted alkane solvents (including cycloalkanes) alcohol solvents, halogenated solvents, aromatic hydrocarbons, esters, ethers, ketones, and combinations thereof. Non-limiting examples of suitable organic solvents are acetonitrile, acetone, allyl alcohol, benzene, butyl acetate, chlorobenzene, chloroform, chloromethane, cyclohexane, cyclopentane, dichloromethane (DCM), dichloroethane, diethyl ether, dimethoxyethane (DME), dimethylformamide (DMF), dimethyl sulfoxide (DMSO), dioxane, ethanol, ethyl acetate, ethylene dichloride, ethylene bromide, formic acid, fluorobenzene, heptane, hexane, isobutylmethylketone, isopropanol, isopropyl acetate, N-methylpyrrolidone, methanol, methylene bromide, methylene chloride, methyl iodide, methylethylketone, methyltetrahydrofuran, pentyl acetate, propanol, n-propyl acetate, sulfolane, tetrahydrofuran (THF), tetrachloroethane, toluene, trichloroethane, water, xylene and combinations thereof. In an exemplary embodiment, a solvent is dichloromethane and acetonitrile. In another exemplary embodiment, a solvent is dichloromethane and acetonitrile in a 1:1 ratio.

The amount of time over which the reaction is conducted may also vary within different embodiments. In some embodiments, the reaction may be conducted over a period of about 10 minutes to about 12 hours. In particular embodiments, the reaction is carried out for about 10 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, or about 12 hours. In an exemplary embodiment, the reaction is conducted for about 1 hour.

The temperature may vary over different embodiments, in some embodiments the temperature may range from about 50° C. to about 100° C. In particular embodiments the temperature may range from about 60° C. to about 90° C., from about 60° C. to about 80° C., from about 70° C. to about 90° C., or from about 80° C. to about 90° C. In an exemplary embodiment, the reaction is conducted at about 80° C.

The synthesized compounds may be used in their crude form or they may be purified. The compounds may be purified by any suitable method known in the art including through column chromatography, crystallization, distillation, extraction, and the like. In one specific embodiment, the solvent is evaporated and the compound is subjected to column purification.

(c) Azido Derivative of MMB to Compound of Formula (I) or (II)

In still another aspect, the method comprises contacting an azido derivative of melampomagnolide B with an acetylenic compound in the presence of copper catalyst, a proton acceptor and a solvent to afford a compound of Formula (I) or (II).

The acetylenic compound may be aromatic, aliphatic or heteroaromatic. The acetylenic compound generally comprises Formula (III): ≡R, wherein R is as described above in Section I(a). Specifically, R is selected from the group consisting of hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, halogen, cyano, nitro, amidine, amino, carboxyl, ester, alkylalkylamino, dialkylamino, hydroxyl, alkoxy or arylalkoxy (e.g. methoxy, ethoxy, benzyloxy, substituted benzyloxy) and combinations thereof.

The mole to mole ratio of azido derivative of MMB to the acetylenic compound can range over different embodiments of the invention. In one embodiment, the ratio of azido derivative of MMB to the acetylenic compound varies from about 0.1:1 to about 1:10. In some embodiments, the mole to mole ratio of azido derivative of MMB to the acetylenic compound is about 0.5:1 to about 1:5. In various embodiments, the mole to mole ratio of azido derivative of MMB to the acetylenic compound is about 0.6:1, about 0.7:1, about 0.8:1, about 0.9:1, about 1:1, about 1:1.1, about 1:1.2, about 1:1.3, about 1:1.4, about 1:1.5, about 1:1.6, about 1:1.7, about 1:1.8, about 1:1.9, or about 1:2. In an exemplary embodiment, the mole to mole ratio of azido derivative of MMB to the acetylenic compound is 1:1.2.

The reaction is carried out in the presence of a copper catalyst. Non-limiting examples of copper catalysts include copper iodide (CuI), copper sulfate ($CuSO_4 \cdot 5H_2O$), copper chloride (CuCl), copper hyposulfite ($CuSO_2 \cdot 5H_2O$), Cu/Fe, $CuBr(PPh_3)_3$, and Cu/C. In a specific embodiment, the copper catalyst is CuI. The mole to mole ratio of azido derivative of MMB to the copper catalyst can range over different embodiments of the invention. In one embodiment, the ratio of azido derivative of MMB to copper catalyst varies from about 1:1 to about 1:0.01. In some embodiments, the mole to mole ratio of azido derivative of MMB to copper catalyst is about 1:1 to about 1:0.1. In various embodiments, the mole to mole ratio of azido derivative of MMB to copper catalyst is about 1:1, about 1:0.9, about 1:0.8, about 1:0.7, about 1:0.6, about 1:0.5, about 1:0.4, about 1:0.3, about 1:0.2, about 1:0.1, or about 1:0.05. In an exemplary embodiment, the mole to mole ratio of azido derivative of MMB to copper catalyst is 1:0.1.

The reaction is preferably carried out in a solvent and is more preferably carried out in an organic solvent. The solvent may be chosen without limitation from including alkane and substituted alkane solvents (including cycloalkanes) alcohol solvents, halogenated solvents, aromatic hydrocarbons, esters, ethers, ketones, and combinations thereof. Non-limiting examples of suitable organic solvents are acetonitrile, acetone, allyl alcohol, benzene, butyl acetate, chlorobenzene, chloroform, chloromethane, cyclohexane, cyclopentane, dichloromethane (DCM), dichloroethane, diethyl ether, dimethoxyethane (DME), dimethylformamide (DMF), dimethyl sulfoxide (DMSO), dioxane, ethanol, ethyl acetate, ethylene dichloride, ethylene bromide, formic acid, fluorobenzene, heptane, hexane, isobutylmethylketone, isopropanol, isopropyl acetate, N-methylpyrrolidone, methanol, methylene bromide, methylene chloride, methyl iodide, methylethylketone, methyltetrahydrofuran, pentyl acetate, propanol, n-propyl acetate, sulfolane, tetrahydrofuran (THF), tetrachloroethane, toluene, trichloroethane, water, xylene and combinations thereof. In an exemplary embodiment, a solvent is water and acetonitrile. In another exemplary embodiment, a solvent is water and acetonitrile in a 1:9 ratio.

A proton acceptor is generally added to facilitate the reaction. The proton acceptor generally has a pKa greater than about 7, or from about 7 to about 13, or more preferably from about 8 to about 10. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In an exemplary embodiment, the proton acceptor is triethylamine.

The amount of time over which the reaction is conducted may also vary within different embodiments. In some embodiments, the reaction may be conducted over a period of about 6 hours to about 36 hours. In particular embodiments, the reaction is carried out for about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, or about 36 hours. In an exemplary embodiment, the reaction is conducted for about 6 hours to about 24 hours.

The temperature may vary over different embodiments, in some embodiments the temperature may range from about 15° C. to about 45° C. In particular embodiments the temperature may range from about 20° C. to about 40° C., from about 25° C. to about 35° C., from about 25° C. to about 30° C., or from about 20° C. to about 30° C. In an exemplary embodiment, the reaction is conducted at about 25° C.

The synthesized compounds may be used in their crude form or they may be purified. The compounds may be purified by any suitable method known in the art including through column chromatography, crystallization, distillation, extraction, and the like. In one specific embodiment, the solvent is evaporated and the compound is subjected to column purification.

III. Method of Use for the Compounds Comprising Formula (I) or (II)

In an aspect, the disclosure provides a method to induce HO-1 expression. The method comprises contacting a cell with a composition comprising a compound of Formula (I) or (II). HO-1 is a human gene that encodes for the enzyme heme oxygenase 1 (EC 1.14.99.3) and may also be referred to as HMOX1, HMOX1D, HO-1, HSP32, bK286B10, and heme oxygenase 1. The cell may be in vitro or in vivo. Methods of measuring protein expression are well known in the art. Additionally, the disclosure provides a method to inhibit the NF-κB pathway. The method comprises contacting a cell with a composition comprising a compound of Formula (I) or (II). The cell may be in vitro or in vivo. Methods of measuring the activity of the NF-κB pathway are known in the art. For example, phosphorylation of the P65 subunit may be measured.

In another aspect, the present disclosure provides a method for inhibiting growth of a cancer cell in a subject. The method comprises administering to the subject a composition comprising a compound of Formula (I) or (II), wherein the amount is effective to inhibit growth of the cancer cell. Cell growth or proliferation can be measured in cells grown in vitro using standard cell viability or cell cytotoxicity assays (e.g., based on DNA content, cell permeability, etc.) in combination with cell counting methods (e.g., flow cytometry, optical density). Cell growth or proliferation can be measured in vivo using imaging procedures and/or molecular diagnostic indicators. In an embodiment, contact with an effective amount of the compound of Formula (I) or (II) selectively inhibits growth of cancer cells. As such, a compound of Formula (I) or (II) does not appreciably kill non-cancer cells at the same concentration. Accordingly, more than 50% of non-cancer cells remain viable following contact with a compound of Formula (I) or (II) at the same concentration. For example about 50%, about 55%, about 60%, about 65%, about 70%, about 75%, about 80%, about 85%, about 90%, about 95% or about 100% of non-cancer cells remain viable following contact with a compound of Formula (I) or (II) at the same concentration. Or, 50%, 55%, 60%, 65%, 70%, 75%, 80%, 85%, 90%, 95% or 100% of non-cancer cells remain viable following contact with a compound of Formula (I) or (II) at the same concentration. In various embodiments, cancer cell growth may be inhibited about 0.5-fold, about 1-fold, about 2-fold, about 3-fold, about 4-fold, about 5-fold, about 8-fold, about 10-fold, or more than 10-fold relative to a reference value. In various other embodiments, cancer cell growth may be inhibited 0.5-fold, 1-fold, 2-fold, 3-fold, 4-fold, 5-fold, 8-fold, 10-fold, or more than 10-fold relative to a reference value. In other embodiments, cancer cell growth may be inhibited to such a degree that the cell undergoes cell death (via apoptosis or necrosis). Any suitable reference value known in the art may be used. For example, a suitable reference value may be the baseline growth rate of the cells as determined by methods known in the art. In another example, a suitable reference value may be a measurement of the number of cancer cells in a reference sample obtained from the same subject. For example, when monitoring the effectiveness of a therapy or efficacy of a compound of Formula (I) or (II), a reference sample may be a sample obtained from a subject before therapy or administration of the compound of Formula (I) or (II) began.

In still another aspect, the present disclosure provides a method of treating, stabilizing or preventing cancer. The method comprises administering to a subject a composition comprising a compound of Formula (I) or (II). By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of a compound of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or in the number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after at least 5, 10, 15, or 20 years.

The compound compositions are as described in Section I above. The subject, the cancer, and the administration of the compositions are described below.

(a) Subject

A method of the disclosure may be used in a subject that is a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc.

(b) Tumor

A compound of the disclosure may be used to treat or recognize a tumor derived from a neoplasm or a cancer. "Neoplasm" is any tissue, or cell thereof, characterized by abnormal growth as a result of excessive cell division. The neoplasm may be malignant or benign, the cancer may be primary or metastatic; the neoplasm or cancer may be early stage or late stage. Non-limiting examples of neoplasms or cancers that may be treated or detected include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In a specific embodiment, the cancer is selected from the group consisting of leukemia, non-small cell lung cancer, colon cancer, CNS cancer, melanoma, ovarian cancer, renal cancer, prostate cancer and breast cancer.

(c) Administration

In certain aspects, a pharmacologically effective amount of a compound of the disclosure may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the peptides useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hem isuccinate, phosphatidyl glycerols and the like.

For therapeutic applications, a therapeutically effective amount of a composition of the invention is administered to a subject. A "therapeutically effective amount" is an amount of the therapeutic composition sufficient to produce a measurable biological tumor response (e.g., a cytotoxic response, or tumor regression). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The timing of administration of the treatment relative to the disease itself and duration of treatment will be determined by the circumstances surrounding the case. Treatment could begin in a hospital or clinic itself, or at a later time after discharge from the hospital or after being seen in an outpatient clinic.

Duration of treatment could range from a single dose administered on a one-time basis to a life-long course of therapeutic treatments. The duration of treatment can and will vary depending on the subject and the disease or disorder to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The frequency of dosing may be once, twice, three times or more daily or once, twice, three times or more per week or per month, or as needed as to effectively treat the symptoms or disease. In certain embodiments, the frequency of dosing may be once, twice or three times daily. For example, a dose may be administered every 24 hours, every 12 hours, or every 8 hours. In other embodiments, the frequency of dosing may be once, twice or three times weekly. For example, a dose may be administered every 2 days, every 3 days or every 4 days. In a different embodiment, the frequency of dosing may be one, twice, three or four times monthly. For example, a dose may be administered every 1 week, every 2 weeks, every 3 weeks or every 4 weeks.

A compound of the present invention, or a composition thereof, may be administered alone or in combination with one or more other pharmaceutical agents, including other compounds of the present invention.

Although the foregoing methods appear the most convenient and most appropriate and effective for administration of peptide constructs, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" as used herein refers to straight or branched chain alkyl groups having in the range of about 1 to about 10 carbon atoms. A substituted alkyl group has one or more substituents as described in the definition of substituted hydrocarbyl. The term "lower alkyl" refers to straight or branched chain alkyl groups having in the range of about 1 to about 4 carbon atoms.

The term "alkylaryl" refers to alkyl substituted aryl groups, and "substituted alkylaryl" refers to alkylaryl groups further bearing one or more substituents.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkoxide" or "alkoxy" as used herein is the conjugate base of an alcohol. The alcohol may be straight chain, branched, cyclic, and includes aryloxy compounds.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl, or substituted naphthyl. The term "substituted aryl" refers to aryl groups bearing or more substituents.

The term "arylalkynyl" refers to aryl-substituted alkynyl groups and "substituted arylalkynyl" refers to arylalkynyl groups further bearing one or more substituents.

The term "aroyl" refers to aryl-substituted species such as benzoyl and "substituted aroyl" refers to aroyl moieties further bearing one or more substituents as set forth above.

The term "cycloalkyl" refers to cyclic ring-containing moieties containing in the range of about 3 up to 7 carbon atoms and "substituted cycloalkyl" refers to cycloalkyl moieties further bearing one or more substituents.

The terms "halide" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and having in the range of 2 up to 12 carbon atoms, or preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thiol.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbamate, carbocyclo, carboxyl, cyano, ester, ether, halogen, heteroaryl, heterocyclo, hydroxyl, keto, ketal, phospho, nitro, thio, trifluoromethyl, sulfonyl, sulfonamide, and the like.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 1B:
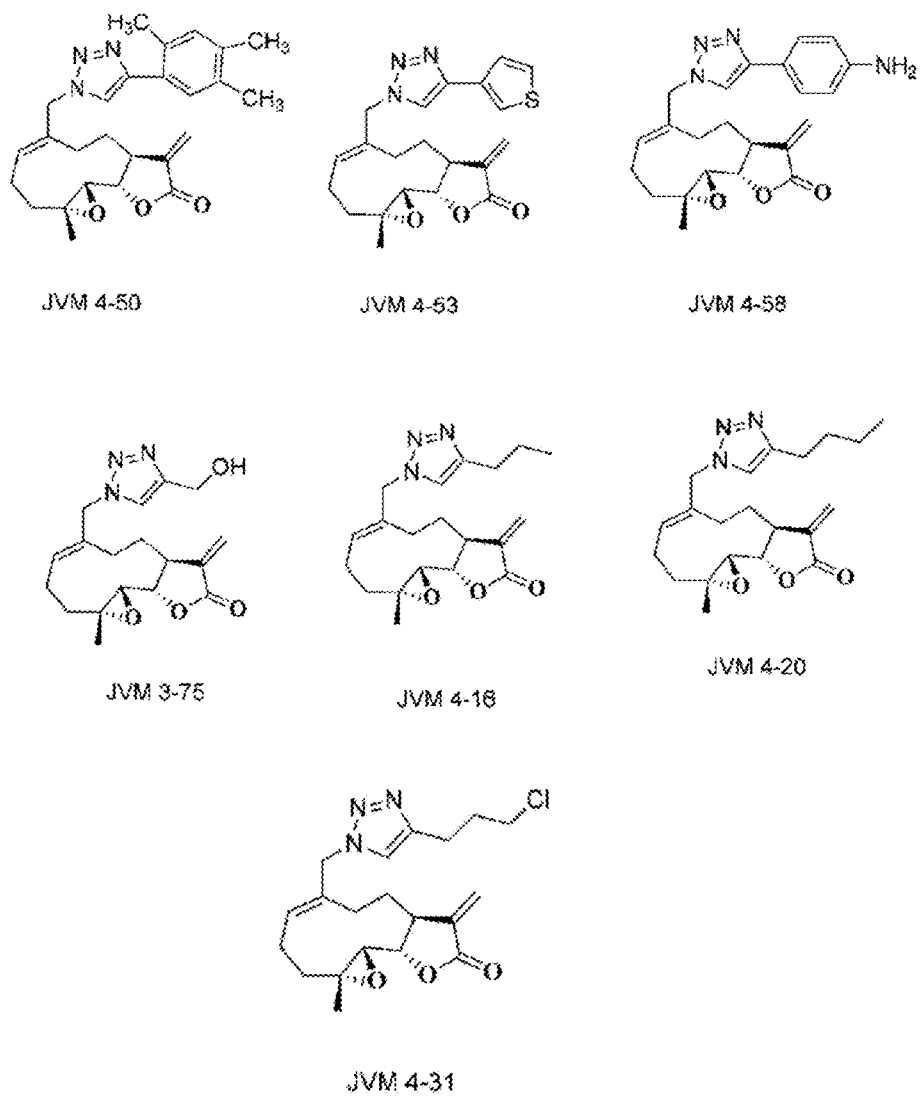
Figure 2A:
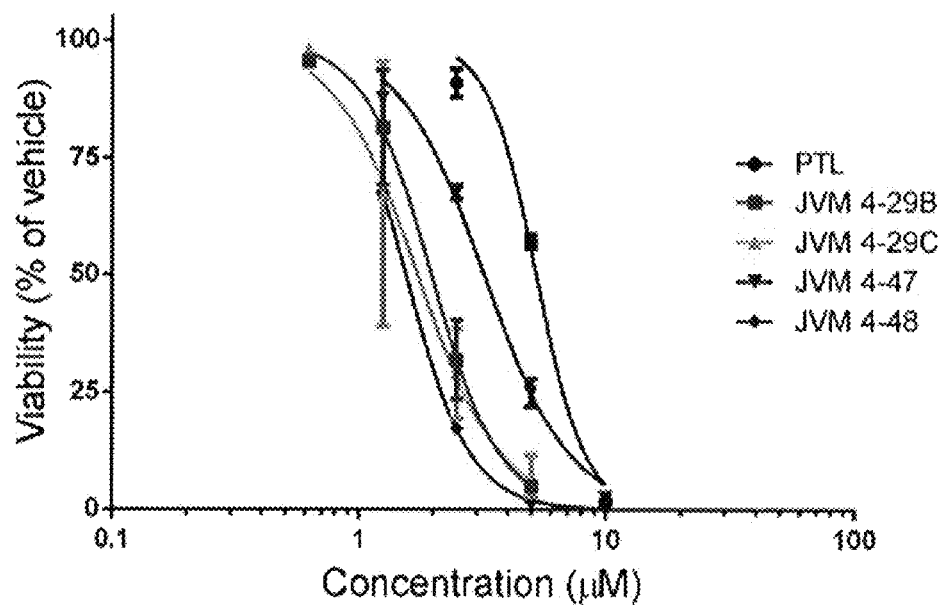
FIG. 2A, FIG. 2B, FIG. 2C, FIG. 2D and FIG. 2E depict the anti-leukemic activity of triazole derivatives of melampomagnolide B against the M9-ENL1 cell line.
Figure 2B:
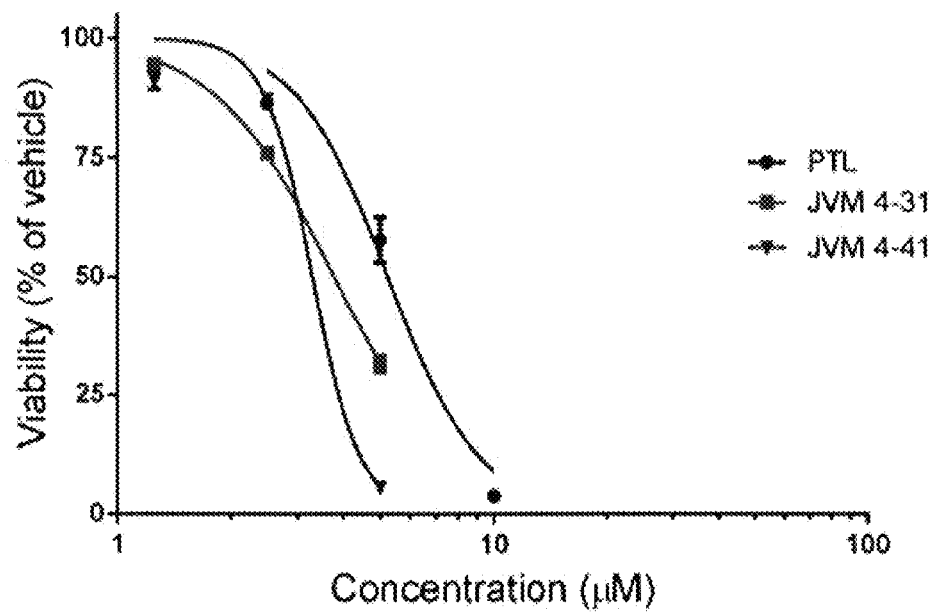
Figure 2C:
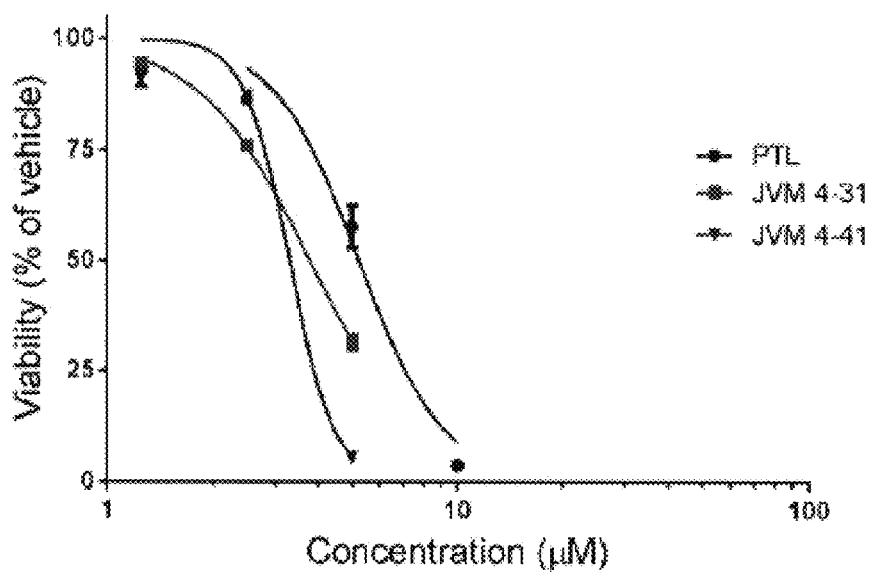
Figure 2D:
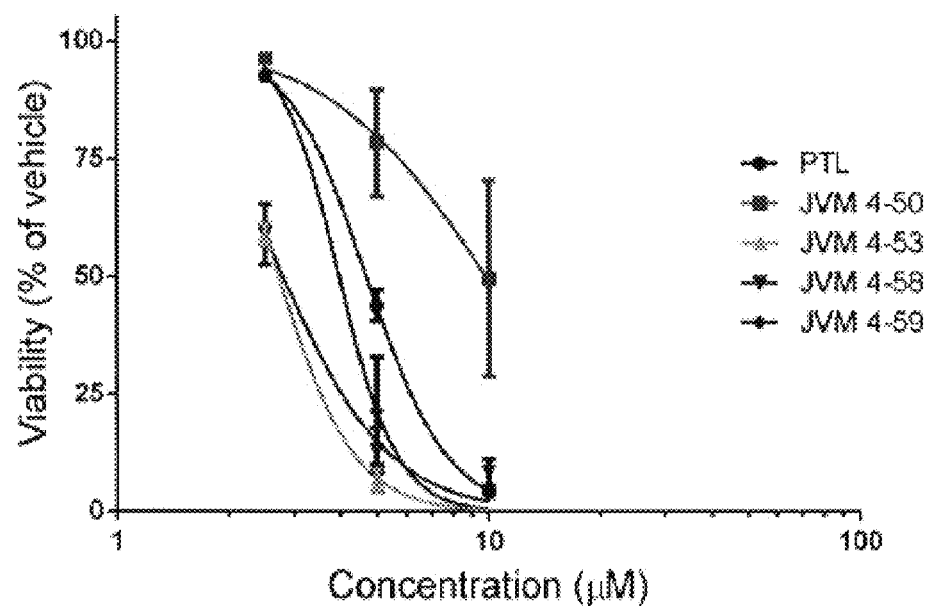
Figure 2E:
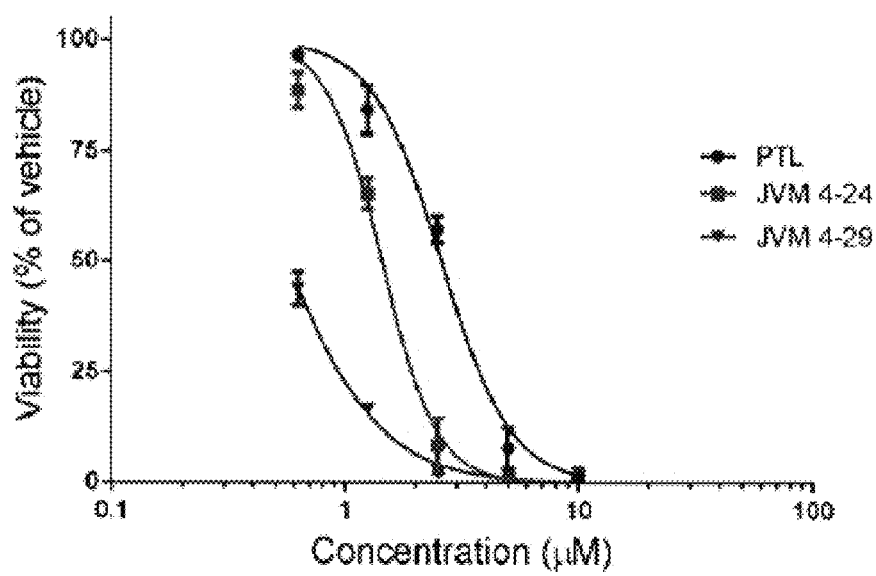
Figures 3A, 3B:
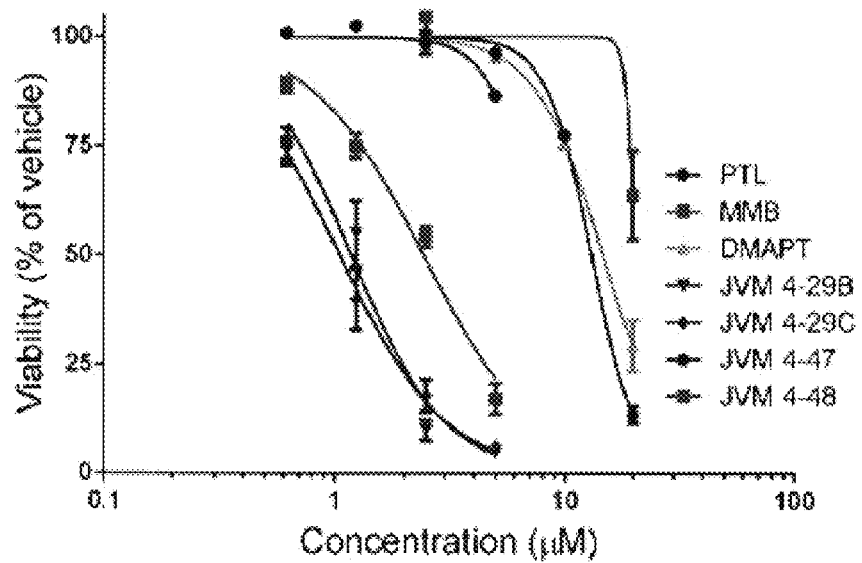
FIG. 3A, FIG. 3B, FIG. 3C and FIG. 3D depict the anti-leukemic activity of triazole derivatives of melampomagnolide B against primary AML.
Figure 3C:
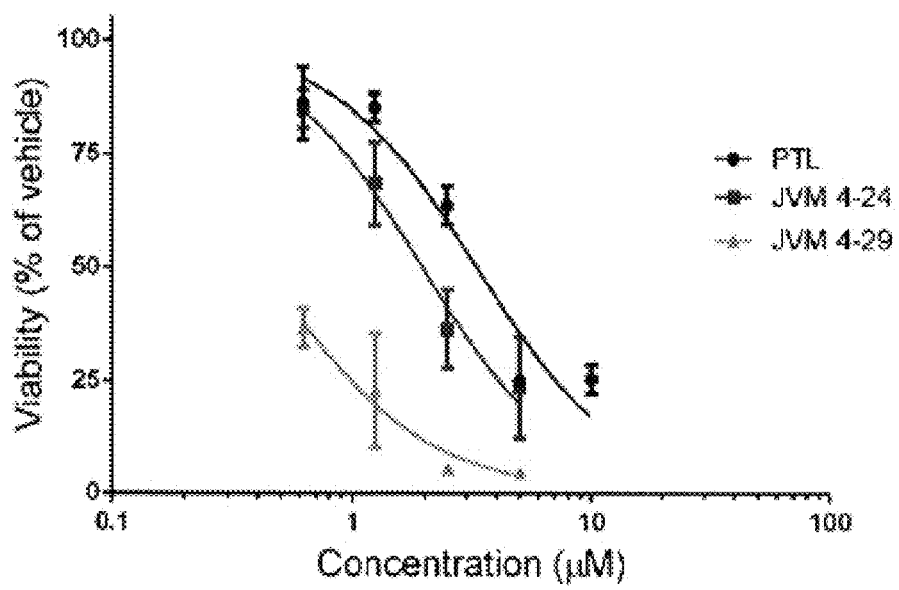
Figure 3D:
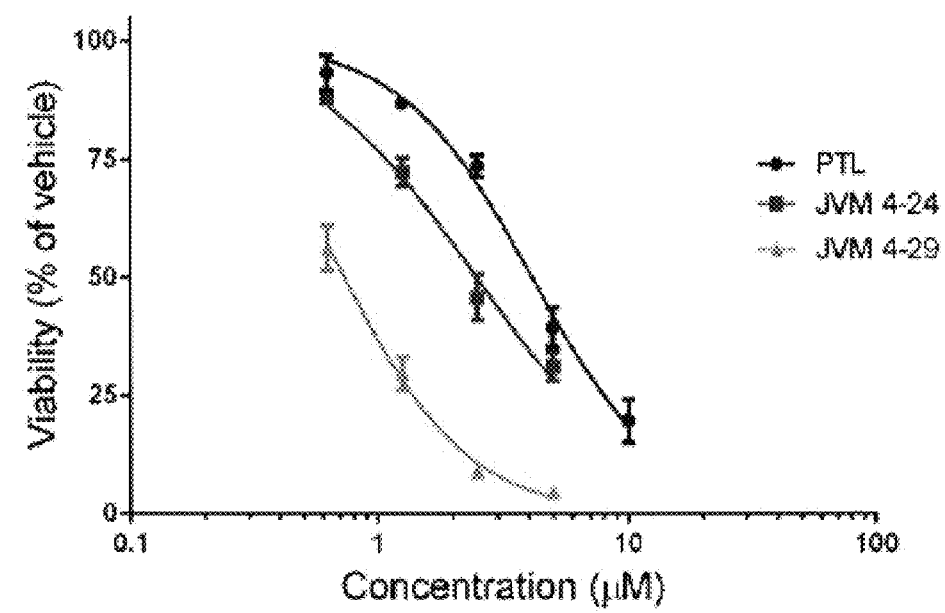

Example 1. Synthetic Schemes for the Preparation of Triazole Derivatives of Melampomagnolide B In the present invention a small library of triazole derivatives of melampomagnolide B was synthesized by reaction of azido derivative (4) with a variety of acetylenic reagents. Initially, the mesylate of MMB (3) was synthesized by reaction of MMB with methane sulfonyl chloride in the presence of triethylamine in dichloromethane. This compound was then reacted with sodium azide in the presence of dimethylformamide and acetonitrile at 80° C. for 1 h to afford the azido derivative (4). The azido derivative of melampomagnolide B was then treated with aromatic, aliphatic and hetero-aromatic acetylenic reagents in the presence of CuI/triethylamine/acetonitrile+water (9:1) at ambient temperature to afford a variety of triazole derivatives of melampomagnolide B (Scheme 1). All these compounds were purified by column chromatography (silica gel; methanol/dichloromethane) to afford analytically pure compounds (FIG. 1A, FIG. 1B) in 60-85% yield. The synthesized compounds were fully characterized by $^1$H NMR and $^{13}$C NMR spectral analysis.

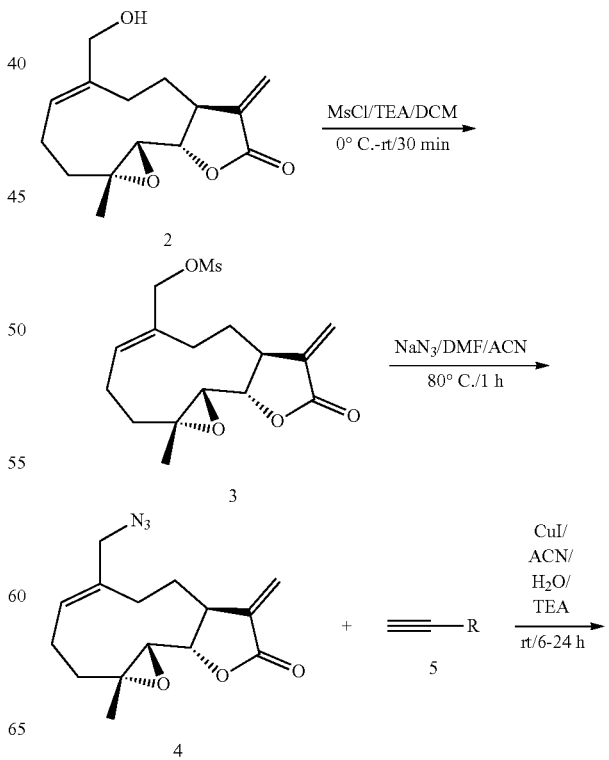

Scheme 1. Synthesis of triazole derivatives of melampomagnolide B.

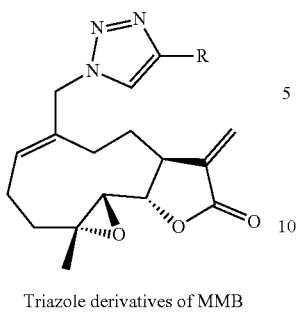

Triazole derivatives of MMB

Among these compounds, JVM 4-29 was identified as a promising anti-cancer agent against both hematological and solid tumor cell lines. To improve the drug-like properties of this compound a dimethylamino adduct as the fumarate salt was prepared (JVM 4-29C, Scheme 2) by reaction of JVM 4-29 with dimethylamine in methanol followed by conversion to the corresponding fumarate salt, which is more water soluble than the free base form. This compound was tested against primary AML and M9 ENL1 cell lines and was observed to have similar cytotoxicity as JVM 4-29.

Scheme 2. Synthesis of dimethyl amino fumarate salt of di-trifluoro methyl phenyl triazole derivative of melampomagnolide B.

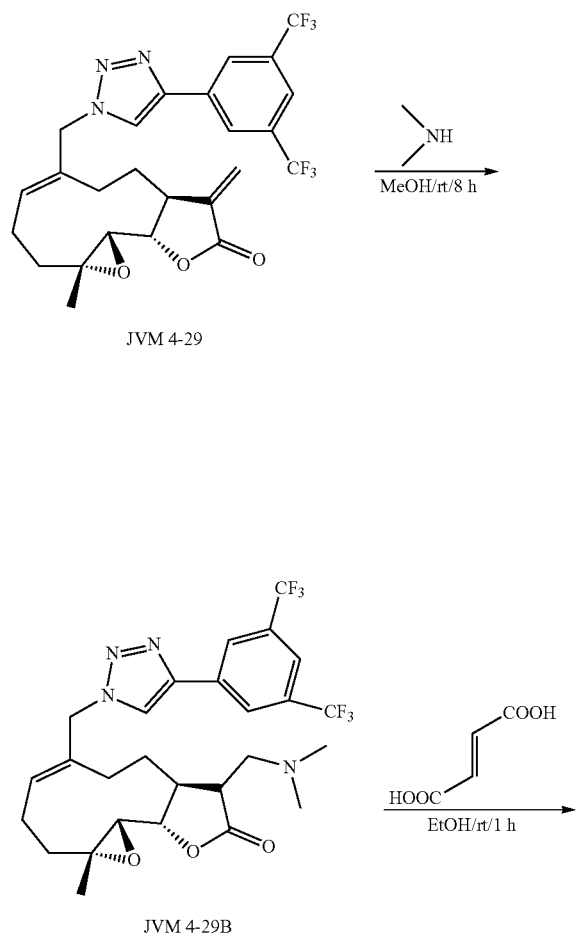

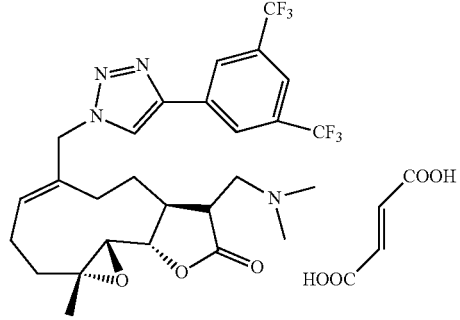

JVM 4-29C

Example 2. Anti-Leukemic Activity of Triazole Derivatives of Melampomagnolide B The newly synthesized triazole derivatives of melampomagnolide B were screened for anti-leukemic activity against M9 ENL1 and primary AML cell lines; the latter were obtained with informed consent from human patients. Evaluations were performed after 24 h of drug exposure using flow cytometric analysis by labeling with Annexin V and 7-aminoactinomycin D (7-AAD) to delineate apoptotic cell populations. In all experiments PTL was included as a reference control. Depending on the potency of the compound, dose-response curves were generated using a concentration range from 0.5-10 µM to determine the concentration resulting in 50% efficacy ($EC_{50}$).

Several compounds exhibited excellent anti-leukemic activity compared to PTL, MMB and DMAPT (Table 1, FIG. 2A-E, FIG. 3A-D). Compound JVM 4-41 exhibited potent anti-cancer activity in ($EC_{50}$=200 nM) against the M9 ENL cell line, and was 26-fold more potent than parthenolide (PTL). Compound JVM 4-29 exhibited 8.6-fold more potent anti-leukemic activity than the PTL against M9 ENL1 cells, 32.7-fold more potent anti-leukemic activity than PTL against primary cell line AML1, and 14.8-fold more potent anti-leukemic activity than the PTL against primary cell line AML2. Similarly, JVM 4-29 was 36.7- and 16.1-fold more cytotoxic compared to DMAPT against AML1 and AML2 primary cell lines. JVM 4-29 was also 51.2- and 34.7-fold more potent than the MMB against AML1 and AML2 primary cell lines. The water soluble analogs of this compound, JVM 4-29B and JVM 4-29C, exhibited similar cytotoxicity against the above cell lines.

Several other analogs exhibited potent anti-leukemic activity. JVM 3-74 ($EC_{50}$=1.9 µM), JVM 4-24 ($EC_{50}$=1.4 µM), JVM 4-27 ($EC_{50}$=1.2 µM), JVM 4-48 ($EC_{50}$=1.5 µM) and JVM 4-58 ($EC_{50}$=2.0 µM) were considered promising anti-leukemic agents against the M9 ENL1 cell line. Compounds JVM 4-25 ($EC_{50}$=1.0, 1.7 µM), JVM 4-26 ($EC_{50}$=1.1, 1.9 µM), JVM 4-24 ($EC_{50}$=2.0, 2.5 µM) and JVM 4-27 ($EC_{50}$=1.3, 1.2 µM) exhibited excellent potency against primary AML1 and AML2 cell lines; these primary AML cells are more resistant to PTL ($EC_{50}$=13.1 and 10.4 µM), DMAPT ($EC_{50}$=14.7 and 11.3 µM) and MMB ($EC_{50}$=20.5 and 24.3 µM).

TABLE 1

The anti-leukemic activity of triazole derivatives of melampomagnolide B against M9 ENL1 and primary AML cell lines.

| S No | Compound | M9ENL1 (EC$_{50}$, μM) | AML#1 (EC$_{50}$, μM) | AML#2 (EC$_{50}$, μM) |
|---|---|---|---|---|
| 1 | JVM 3-74 | 1.9 | ND | ND |
| 2 | JVM 3-75 | 38 | ND | ND |
| 3 | JVM 3-76 | 11 | ND | ND |
| 4 | JVM 4-25 | ND | 1.0 | 1.7 |
| 5 | JVM 4-26 | ND | 1.1 | 1.9 |
| 6 | JVM 4-24 | 1.4 | 2.0 | 2.5 |
| 7 | JVM 4-27 | 1.2 | 1.3 | 1.2 |
| 8 | JVM 4-29 | 0.6 | 0.4 | 0.7 |
| 9 | JVM 4-42 | ND | ND | ND |
| 10 | JVM 4-41 | 0.2 | ND | ND |
| 11 | JVM 4-47 | 3.2 | 7.9 | ND |
| 12 | JVM 4-48 | 1.5 | 2.4 | ND |
| 13 | JVM 4-50 | 9.8 | ND | ND |
| 14 | JVM 4-53 | 2.7 | ND | ND |
| 15 | JVM 4-58 | 2.0 | ND | ND |
| 16 | JVM 4-59 | 3.9 | ND | ND |
| 17 | JVM 4-16 | 5.5 | ND | ND |
| 18 | JVM 4-20 | 4.3 | ND | ND |
| 19 | JVM 4-31 | 3.8 | ND | ND |
| 20 | JVM 4-29B | 1.9 | 1.1 | 2.3 |
| 21 | JVM 4-29C | 1.7 | 1.0 | 2.9 |
| 22 | PTL | 5.2 | 13.1 | 10.4 |
| 23 | DMAPT | 6 | 14.7 | 11.3 |
| 24 | MMB | 16 | 20.5 | 24.3 |

The EC$_{50}$ values <2 μM are bolded.
ND: Not determined.

Example 3. Mechanism of Action Studies of MMB Triazole Compounds

Figure 4A:
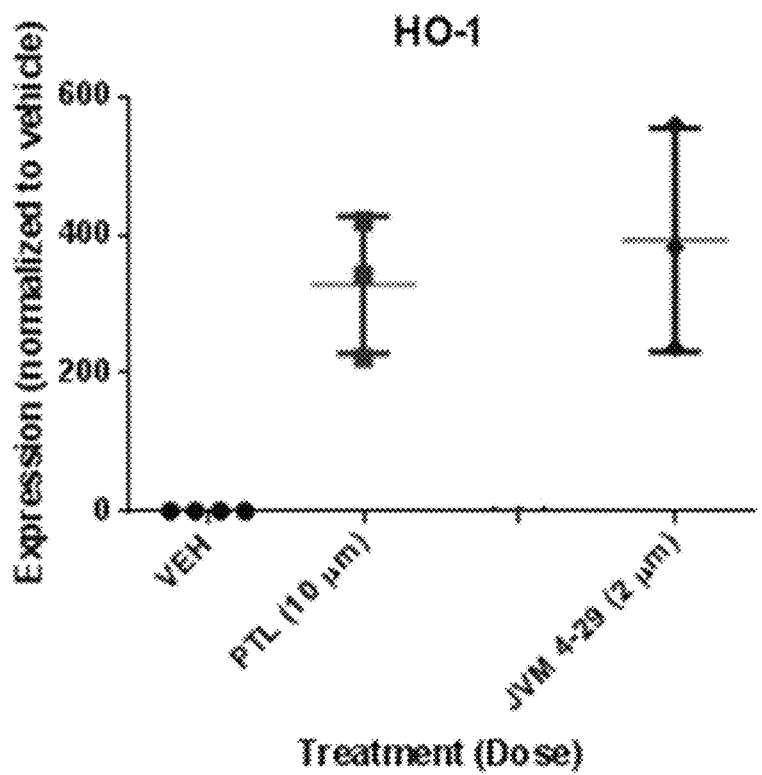
FIG. 4A and FIG. 4B depict a graph an immunoblot showing a comparative study of JVM 4-29 and PTL in induction of HO-1 by using Western blot assay.
Figure 4B:
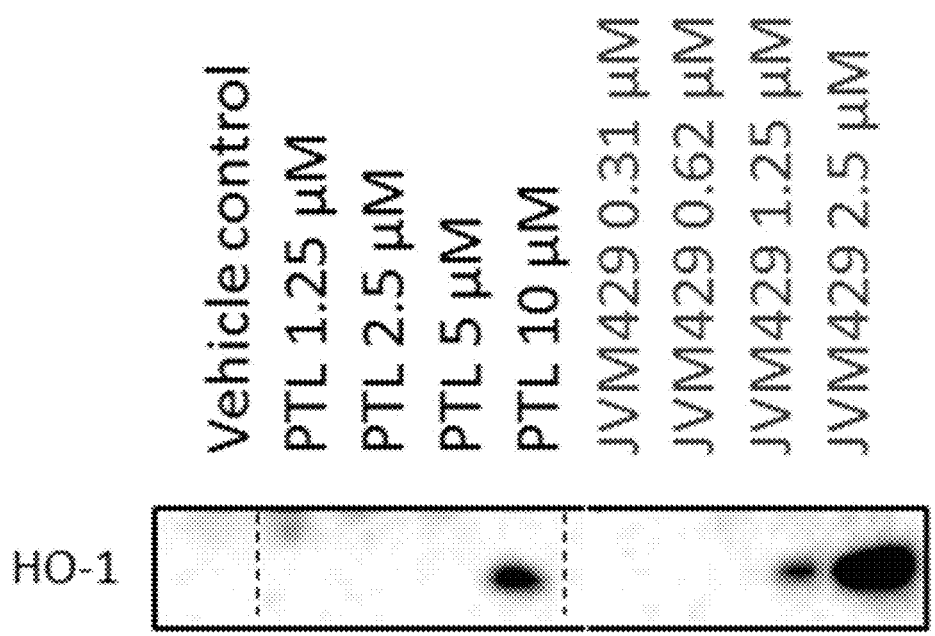
Figure 5:
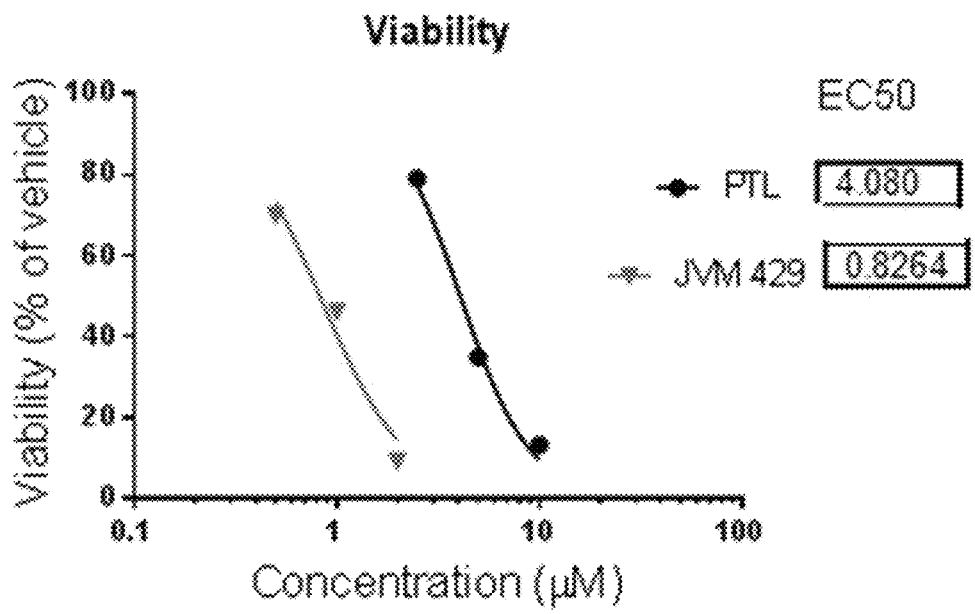
FIG. 5 depicts a graph showing the viability ($EC_{50}$) of JVM 4-29 and PTL against M9 ENL1 cells in culture.

The most active compound JVM 4-29 was studied for induction of HO-1 by Western blot assay and comparing its toxicity with parthenolide. The results indicate that JVM 4-29 exhibits stronger induction of HO-1 when compared to PTL (FIG. 4A, FIG. 4B) and is more cytotoxic than parthenolide in the M9 ENL1 cell assay (FIG. 5).

Figure 6:
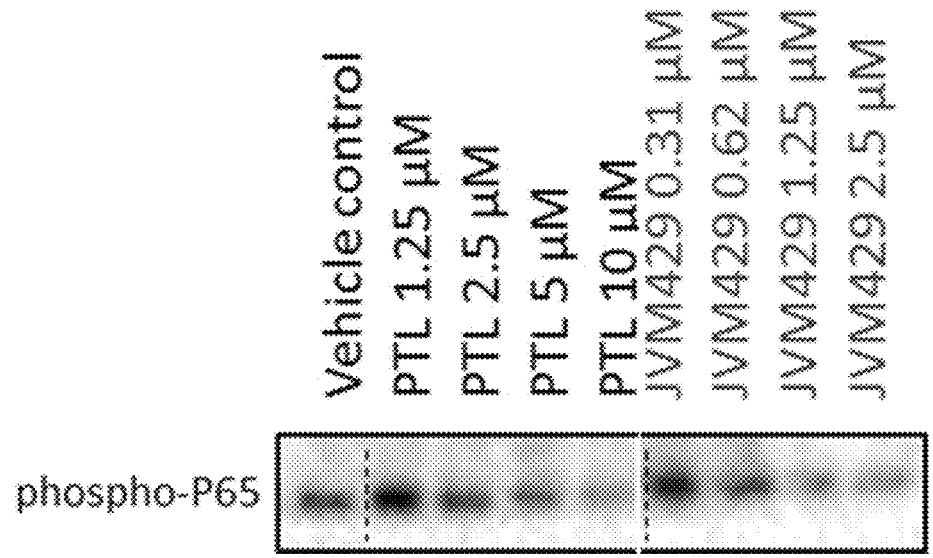
FIG. 6 depicts an immunoblot showing NF-kB inhibition studies with JVM 4-29 and PTL.

Also JVM 4-29 was evaluated for NF-κB inhibition by Western blot analysis; by determining its effect on the phosphorylation of the P65 subunit. JVM 4-29 showed significantly more potency as an inhibitor of the NF-κB pathway when compared to parthenolide (FIG. 6).

Example 4. Anti-Cancer Activity of Triazole Derivatives of Melampomagnolide B The above triazole derivatives of melampomagnolide B were evaluated for growth inhibitory properties against an NCI panel of 60 human cancer cell lines derived from nine human cancer cell types, grouped into disease sub-panels that represent leukemia, lung, colon, central nervous system (CNS), melanoma, renal, ovary, breast, and prostate cancer cells. Growth inhibitory (GI$_{50}$) effects were measured as a function of the variation of optical density as a percentage of control. The compounds were first screened at a single concentration of $10^{-5}$ M. Compounds which showed more than 60% growth inhibition in at least eight of the sixty cell lines in the panel were selected for a complete dose response study with five different concentrations ($10^{-4}$ M, $10^{-5}$ M, $10^{-6}$ M, $10^{-7}$ M and $10^{-8}$ M) of drug. Based on the preliminary screening results, 6 compounds: JVM 3-74, JVM 4-16, JVM 4-24, JVM 4-25, JVM 4-26, JVM 4-29 and JVM 4-50 were selected for five-dose testing and several of these compounds exhibited potent anti-cancer activity (Table 2). Among these compounds, two analogs: JVM 4-25 and JVM 4-29 exhibited potent growth inhibition (GI$_{50}$) against all the cell lines in the leukemia sub-panel in the nanomolar concentration range (100-500 nm). Compound JVM 4-29 was identified as the lead compound in this series since it exhibited a GI$_{50}$ value of 27 nm against the RXF 393 renal cancer cell line. JVM 4-29 also exhibited potent growth inhibition against most of the solid tumor cell lines in the panel (GI$_{50}$=120-880 nm). A second compound, JVM 4-25, also exhibited cytotoxicity in the nanomolar concentration range (GI$_{50}$=160-990 nm) against most of the solid tumor cell lines in the NCI 60 human cancer cell panel. A third compound, JVM 4-26, exhibited good potency against leukemia cell lines CCRF-CEM, HL-60(TB), K-562, MOLT-4 and SR with growth inhibition values in the nanomolar range (240-940 nm). This compound also exhibited potent growth inhibition in the nanomolar range (180-940 nm) against most of the solid tumor cell lines in the NCI panel. Compounds JVM 3-74, JVM 4-24 and JVM 4-50 exhibited good cytotoxicity against several cell lines in the NCI 60 cell panel with GI$_{50}$ values in the nanomolar range (200-990 nm). JVM 4-16 exhibited anti-cancer activity in the low micromolar concentration range (GI$_{50}$<5 μM) against several cell lines in the panel.

TABLE 2

Growth inhibition (GI50) data for triazole derivatives of melampomagnolide B against a panel of 60 human cancer cell types.

| Panel | Cell line | JVM 3-74 | JVM 4-16 | JVM 4-24 | JVM 4-25 | JVM 4-26 | JVM 4-29 | JVM 4-50 |
|---|---|---|---|---|---|---|---|---|
| | | | | GI$_{50}^{a}$ (μm) | | | | |
| Leukemia | CCRF-CEM | 0.99 | 3.00 | 0.29 | 0.20 | 0.24 | 0.69 | 0.45 |
| | HL-60(TB) | 1.49 | 3.53 | 1.17 | 0.33 | 0.72 | 0.19 | 0.64 |
| | K-562 | 1.76 | 3.96 | 1.30 | 0.40 | 0.94 | 0.23 | 1.39 |
| | MOLT-4 | 1.29 | 5.54 | 1.13 | 0.31 | 0.38 | 0.19 | 2.38 |
| | RPMI-8226 | 1.71 | 5.52 | 1.87 | 0.50 | 1.41 | 0.22 | 1.18 |
| | SR | 1.06 | 2.88 | 0.25 | 0.23 | 0.25 | 0.10 | 1.26 |
| Non-Small Cell Lung Cancer | A549/ATCC | 5.88 | 22.3 | 10.9 | 1.79 | 3.37 | 1.36 | 1.73 |
| | EKVX | 6.87 | 11.5 | 2.47 | 1.57 | 1.49 | 1.50 | 1.22 |
| | HOP-62 | 7.41 | 14.1 | 10.5 | 1.94 | 3.04 | 1.56 | 1.77 |
| | HOP-92 | 1.42 | 2.94 | 1.13 | 0.25 | 0.34 | 0.34 | 0.43 |
| | NCI-H226 | 4.60 | 12.6 | 1.99 | 1.71 | 2.48 | 1.65 | 1.46 |
| | NCI-H23 | 5.38 | 13.6 | 2.06 | 1.58 | 1.78 | 1.12 | 1.77 |
| | NCI-H322M | 7.79 | 21.5 | 10.7 | 2.17 | 4.39 | 1.67 | 11.1 |
| | NCI-H460 | 7.74 | 21.2 | 8.45 | 2.13 | 3.66 | 1.22 | 3.16 |
| | NCI-H522 | 0.81 | 3.06 | 0.38 | 0.29 | 0.25 | 0.12 | 0.28 |
| Colon Cancer | COLO 205 | 1.08 | 5.22 | 0.50 | 0.41 | 0.45 | 0.14 | 0.64 |
| | HCC-2998 | 6.16 | 15.1 | 1.98 | 1.64 | 1.74 | 1.17 | 1.72 |

TABLE 2-continued

Growth inhibition (GI50) data for triazole derivatives of melampomagnolide B against a panel of 60 human cancer cell types.

| Panel | Cell line | JVM 3-74 | JVM 4-16 | JVM 4-24 | JVM 4-25 | JVM 4-26 | JVM 4-29 | JVM 4-50 |
|---|---|---|---|---|---|---|---|---|
| | | | | | $GI_{50}^{a}$ (μm) | | | |
| | HCT-116 | 1.17 | 3.98 | 0.48 | 0.16 | 0.29 | 0.15 | 0.33 |
| | HCT-15 | 0.77 | 2.90 | 0.33 | 0.19 | 0.28 | 0.19 | 0.20 |
| | HT-29 | 1.79 | 5.50 | 1.23 | 0.51 | 0.69 | 0.19 | 0.50 |
| | KM12 | 8.48 | 17.6 | 3.51 | 1.78 | 1.70 | 1.04 | 2.31 |
| | SW-620 | 1.50 | 4.23 | 0.49 | 0.33 | 0.42 | 0.19 | 0.42 |
| CNS Cancer | SF-268 | 5.63 | 13.7 | 2.07 | 1.59 | 1.69 | 1.08 | 1.52 |
| | SF-295 | 7.89 | 18.5 | 11.0 | 3.41 | 5.73 | 1.19 | 6.44 |
| | SF-539 | 2.01 | 8.87 | 0.34 | 0.25 | 0.27 | 0.17 | 0.52 |
| | SNB-19 | 7.87 | 18.8 | 6.92 | 2.40 | 3.39 | 1.71 | 3.90 |
| | SNB-75 | 6.21 | 18.5 | 1.47 | 1.16 | 1.25 | 1.26 | 0.52 |
| | U251 | 7.96 | 14.1 | 9.45 | 1.61 | 2.02 | 1.44 | 1.53 |
| Melanoma | LOX IMVI | 0.80 | 3.91 | 1.16 | 0.28 | 0.90 | 0.15 | 0.72 |
| | MALME-3M | 1.17 | 4.70 | 1.67 | 1.20 | 1.40 | 0.52 | 1.43 |
| | M14 | 1.78 | 3.99 | 1.30 | 0.79 | 0.94 | 0.35 | 1.50 |
| | MDA-MB-435 | 2.37 | 10.4 | 1.14 | 0.59 | 1.00 | 0.74 | 1.41 |
| | SK-MEL-2 | 5.50 | 16.3 | 1.95 | 1.66 | 1.83 | 0.34 | 1.75 |
| | SK-MEL-28 | 1.06 | ND | 0.82 | 0.35 | 0.82 | 0.46 | 1.40 |
| | SK-MEL-5 | 7.32 | 15.3 | 2.10 | 1.70 | 1.74 | 1.47 | 1.66 |
| | UACC-257 | 3.78 | ND | 1.78 | 1.42 | 1.47 | 1.46 | 1.29 |
| | UACC-62 | 1.87 | ND | 1.35 | 0.62 | 1.26 | 0.34 | 1.13 |
| Ovarian Cancer | IGROV1 | 6.95 | 4.63 | 1.35 | 0.73 | 1.17 | 0.84 | 1.29 |
| | OVCAR-3 | 1.40 | 3.96 | 0.56 | 0.47 | 0.49 | 0.15 | 1.03 |
| | OVCAR-4 | 3.22 | 9.46 | 1.52 | 1.09 | 1.29 | 0.50 | 0.70 |
| | OVCAR-5 | 5.70 | 14.1 | 1.71 | 1.21 | 1.47 | 1.10 | 1.74 |
| | OVCAR-8 | 2.31 | 13.5 | 2.59 | 1.31 | 1.66 | 0.88 | 0.92 |
| | NCI/ADR-RES | 6.17 | 15.2 | 3.08 | 2.39 | 3.05 | 1.05 | 2.51 |
| | SK-OV-3 | 9.95 | 26.0 | 16.3 | 3.67 | 9.78 | 1.86 | 11.7 |
| Renal Cancer | 786-0 | 2.63 | 11.3 | 1.24 | 0.50 | 1.06 | 0.16 | 1.50 |
| | A498 | 7.80 | 21.5 | 2.35 | 1.52 | 1.82 | 0.43 | 1.04 |
| | ACHN | 0.94 | 3.81 | 0.29 | 0.18 | 0.18 | 0.16 | 1.07 |
| | CAKI-1 | 1.28 | 3.91 | 1.03 | 0.86 | 1.03 | ND | 1.08 |
| | RXF 393 | 1.55 | 4.80 | 0.70 | 0.55 | 0.87 | 0.02 | 0.96 |
| | SN12C | 4.50 | 12.1 | 1.96 | 1.40 | 1.64 | 0.70 | 1.49 |
| | TK-10 | 1.21 | 3.86 | 1.42 | 0.99 | 1.24 | ND | 1.46 |
| | UO-31 | 0.87 | 11.1 | 1.27 | 1.08 | 1.22 | 0.38 | 0.52 |
| Prostate Cancer | PC-3 | 5.65 | 14.9 | 9.35 | 1.98 | 2.00 | 0.83 | 1.47 |
| | DU-145 | 2.19 | 4.32 | 1.11 | 1.00 | 0.69 | 0.72 | 1.35 |
| Breast Cancer | MCF7 | 1.08 | 3.35 | 0.42 | 0.31 | 0.35 | 0.19 | 0.43 |
| | MDA-MB-231/ATCC | 2.00 | 4.22 | 1.44 | 1.09 | 1.22 | 0.33 | 1.11 |
| | HS 578T | 9.78 | 23.4 | 7.42 | 2.26 | 3.68 | 1.03 | 1.94 |
| | BT-549 | 2.65 | 14.2 | 1.31 | 0.77 | 0.83 | 0.17 | 0.75 |
| | T-47D | 1.30 | 4.11 | 1.43 | 0.83 | 0.74 | 0.33 | 0.53 |
| | MDA-MB-468 | 0.95 | 3.65 | 0.89 | 0.56 | 0.42 | 0.42 | 0.53 |

[a]$GI_{50}$: 50% Growth inhibition, concentration of drug resulting in a 50% reduction in net protein increase compared with control cells.
ND: Not determined,
$GI_{50}$ values <1 μm are bolded.

TABLE 3

Growth inhibition (GI50) data for triazole derivatives of melampomagnolide B against a panel of 60 human cancer cell types.

| Panel/cell line | JVM 4-53 $GI_{50}^{a}$ (μM) | JVM 4-58 $GI_{50}^{a}$ (μM) | JVM 4-59 $GI_{50}^{a}$ (μM) |
|---|---|---|---|
| Leukemia | | | |
| CCRF-CEM | 1.63 | 2.0 | 0.76 |
| HL-60 (TB) | 1.91 | 2.23 | 2.58 |
| K-562 | 2.51 | 2.99 | 2.40 |
| MOLT-4 | 2.59 | 2.87 | 3.03 |
| RPMI-8226 | 2.45 | 2.75 | 1.87 |
| SR | 0.56 | 0.70 | 0.81 |
| Non-Small Cell Lung Cancer | | | |
| A549/ATCC | 8.61 | 11.9 | 7.23 |
| EKVX | 2.33 | 3.89 | 2.32 |
| HOP-62 | 4.90 | 10.2 | 4.73 |
| HOP-92 | 1.66 | 2.13 | 1.48 |
| NCI-H226 | 2.09 | 3.34 | 1.73 |
| NCI-H23 | 1.82 | 2.49 | 1.75 |
| NCI-H322M | 10.5 | 12.6 | 10.8 |
| NCI-H460 | 4.71 | 10.4 | 3.97 |
| NCI-H522 | 1.39 | 1.37 | 1.38 |
| Colon Cancer | | | |
| COLO 205 | 1.45 | 1.79 | 1.98 |
| HCC-2998 | 1.84 | 3.49 | 1.85 |
| HCT-116 | 1.16 | 1.55 | 1.26 |
| HCT-15 | 1.11 | 1.42 | 1.05 |

TABLE 3-continued

Growth inhibition (GI$_{50}$) data for triazole derivatives of melampomagnolide B against a panel of 60 human cancer cell types.

| Panel/cell line | JVM 4-53 GI$_{50}$[a] (μM) | JVM 4-58 GI$_{50}$[a] (μM) | JVM 4-59 GI$_{50}$[a] (μM) |
|---|---|---|---|
| HT29 | 1.66 | 2.14 | 1.79 |
| KM12 | 6.45 | 11.4 | 5.88 |
| SW-620 | 1.32 | 2.16 | 1.24 |
| CNS Cancer | | | |
| SF-268 | 2.53 | 3.70 | 2.09 |
| SF-295 | 9.61 | 12.1 | 10.3 |
| SF-539 | 1.80 | 2.77 | 1.76 |
| SNB-19 | 9.49 | 12.7 | 10.8 |
| SNB-75 | 3.23 | 4.98 | 2.97 |
| U251 | 2.50 | 4.16 | 1.83 |
| Melanoma | | | |
| LOX IMVI | 1.28 | 1.51 | 1.11 |
| MALME-3M | 1.61 | 2.18 | 1.70 |
| M14 | 1.93 | 2.97 | 2.15 |
| MDA-MB-435 | 1.85 | 3.01 | 2.18 |
| SK-MEL-2 | 2.27 | 10.6 | 2.45 |
| SK-MEL-28 | 1.81 | 2.71 | 1.75 |
| SK-MEL-5 | 1.83 | 3.47 | 1.72 |
| Ovarian Cancer | | | |
| IGROV1 | 1.92 | 2.96 | 1.81 |
| OVCAR-3 | 1.06 | 1.62 | 1.04 |
| OVCAR-4 | 2.48 | 4.90 | 2.77 |
| OVCAR-5 | 2.29 | 6.43 | 2.46 |
| OVCAR-8 | 2.96 | 3.04 | 2.23 |
| NCI/ADR-RES | 3.79 | 14.5 | 2.99 |
| SK-OV-3 | 17.4 | 18.3 | 17.3 |
| Renal Cancer | | | |
| 786-0 | 1.76 | 1.98 | 1.84 |
| A498 | 2.65 | 10.4 | 3.86 |
| ACHN | 1.32 | 2.65 | 1.45 |
| CAKI-1 | 1.06 | 1.77 | 1.31 |
| RXF 393 | 1.07 | 1.41 | 1.07 |
| SN12C | 2.45 | 3.48 | 2.47 |
| TK-10 | 1.52 | 2.25 | 1.71 |
| UO-31 | 1.35 | 1.87 | 1.23 |
| Prostate Cancer | | | |
| PC-3 | 4.21 | 10.1 | 4.32 |
| DU-145 | 1.43 | 3.65 | 1.42 |
| Breast Cancer | | | |
| MCF7 | 1.68 | 2.41 | 1.33 |
| MDA-MB-231/ATCC | 1.75 | 3.45 | 1.64 |
| HS 578T | 2.82 | 4.46 | 3.57 |
| BT-549 | 1.80 | 3.05 | 2.40 |
| T-47D | 2.03 | 2.23 | 1.70 |
| MDA-MB-468 | 1.28 | 1.77 | 1.14 |

[a]GI$_{50}$: 50% Growth inhibition, concentration of drug resulting in a 50% reduction in net protein increase compared with control cells.
ND: Not determined.
GI$_{50}$ values <1 μm are bolded.

Example 5. General Synthetic Methods for Triazole Derivatives of Melampomagnolide B To obtain the triazole derivatives of melampomagnolide B, all synthetic reactions were carried out at ambient temperature and the products were purified by flash column chromatography (silica gel; methanol/dichloromethane) to afford pure compounds in 60-85% yield. $^1$H and $^{13}$C NMR spectra were recorded on a Varian 400 MHz spectrometer equipped with a Linux workstation running on vNMRj software.

Synthetic Procedure and Analytical Data for the Azido Compound of Melampomagnolide B (4):

To melampomagnolide B (300 mg, 1.13 mmol) in dichloromethane (5 mL), triethylamine (0.158 mL, 1.13 mmol) and methane sulfonyl chloride (129.3 mg, 1.13 mmol) were added at 0° C. The reaction mixture was stirred at 0° C. for 30 min. After completion of the reaction, water was added and the mixture was extracted with dichloromethane. The organic layer was washed with water (3×10 mL), dried over Na$_2$SO$_4$ and concentrated under reduced pressure to afford MMB mesylate. To MMB mesylate (360 mg, 1.05 mmol) in acetonitrile/DMF (1:1) 10 mL, sodium azide (136.8 mg, 2.10 mmol) was added. The reaction mixture was heated at 80° C. for 1 h. After completion of the reaction, the solvent was evaporated under reduced pressure and the crude residue was subjected to column purification (silica gel, 30-40% EtOAc in hexane) to afford the pure azido analog 4 as white solid (200 mg, 61%).

$^1$H NMR (CDCl$_3$, 400 MHz): (δ 6.27 (d, J=3.6 Hz, 1H), 5.67 (t, J=8.0 Hz, 1H), 5.55 (d, J=3.6 Hz, 1H), 3.87-3.81 (m, 2H), 3.70 (d, J=13.2 Hz, 1H), 2.85 (d, J=9.6 Hz, 1H), 2.76-2.69 (m, 1H), 2.49-2.16 (m, 6H), 1.74-1.66 (m, 1H), 1.55 (s, 3H), 1.12 (t, J=12 Hz, 1H). $^{13}$C NMR (CDCl$_3$, 100 MHz) δ 169.3, 138.7, 134.8, 131.3, 120.5, 81.0, 63.4, 60.0, 55.7, 42.8, 36.7, 25.5, 24.2, 23.9, 18.1 ppm.

General Synthetic Procedure and Analytical Data for the Triazole Derivatives of Melampomagnolide B:

To the azido compound of melampomagnolide (4, 60 mg, 0.20 mmol) in acetonitrile and water (9:1) (3 mL), the appropriate acetylenic reagent (0.248 mmol) and copper iodide (3.8 mg, 0.02 mmol) were added. The reaction mixture was stirred for 6-24 h. After completion of the reaction, the solvent was evaporated under reduced pressure to afford a crude reaction mass. To this crude reaction mass, water was added and the mixture extracted with EtOAc. The organic layer was washed with water (2×5 mL), dried over anhydrous Na$_2$SO$_4$, filtered, and the solvent removed to afford the crude reaction product. The crude product was purified by column chromatography (silica gel, 2-5% methanol in dichloromethane) to afford the appropriate triazole derivative of melampomagnolide (yield: 60-85%).

Example 6. (1aR,7aS,10aS,10bS,E)-5-((4-(3,5-bis(Trifluoromethyl)phenyl)-1H-1,2,3-triazol-1-yl)methyl)-1a-methyl-8-methylene-2,3,6,7,7a,8,10a,10b-octahydrooxireno[2',3':9,10]cyclodeca[1,2-b]furan-9(1aH)-one (JVM 4-29)

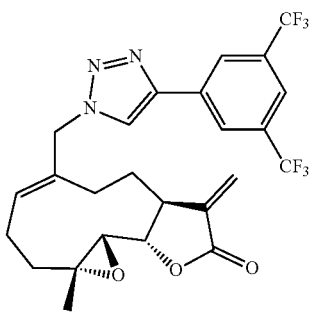 [SMILES: C=C1C(=O)O[C@H]2[C@H]1CC/C(Cn1cc(-c3cc(C(F)(F)F)cc(C(F)(F)F)c3)nn1)=C\CC[C@@]1(C)O[C@@H]21]

$^1$H NMR (CDCl$_3$, 400 MHz): δ 8.29 (s, 2H), 7.91 (s, 1H), 7.84 (s, 1H), 6.33 (d, J=3.6 Hz, 1H), 5.83 (t, J=8 Hz, 1H), 5.71 (d, J=2.8 Hz, 1H), 5.31 (d, J 14.8 Hz, 1H), 4.82 (d, J=14.8 Hz, 1H), 3.87 (t, J=9.2 Hz, 1H), 2.89-2.81 (m, 2H), 2.69-2.62 (m, 1H), 2.51-2.20 (m, 4H), 1.99 (d, J 10.4 Hz, 1H), 1.69 (t, J=11.6 Hz, 1H), 1.55 (s, 3H), 1.17 (t, J=10 Hz,

1H). $^{13}$C NMR (CDCl$_3$, 100 MHz) δ 169.2, 145.7, 138.2, 134.9, 132.7, 132.6, 132.6, 132.3, 125.7, 124.6, 121.9, 121.8, 121.1, 120.4, 80.9, 63.4, 59.9, 55.2, 42.7, 36.5, 25.2, 24.2, 23.6, 18.0 ppm.

Example 7. (1aR,7aS,10aS,10bS,E)-5-((4-(3,5-Difluorophenyl)-1H-1,2,3-triazol-1-yl)methyl)-1a-methyl-8-methylene-2,3,6,7,7a,8,10a,10b-oetahydrooxireno[2',3':9,10]cyclodeca[1,2-b]furan-9(1aH)-one (JVM 4-48)

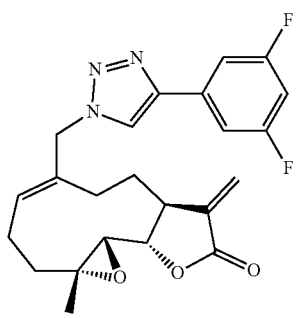 [SMILES: C=C1C(=O)O[C@H]2[C@H]1CC/C(Cn1cc(-c3cc(F)cc(F)c3)nn1)=C\CC[C@@]1(C)O[C@@H]21]

$^1$H NMR (CDCl$_3$, 400 MHz): δ 7.75 (s, 1H), 7.38-7.33 (m, 2H), 6.78 (t, J=9.2, 2.4 Hz, 1H), 6.32 (d, J=3.2 Hz, 1H), 5.81 (t, J=8 Hz, 1H), 5.69 (d, 1H), 5.26 (d, J=14.8 Hz, 1H), 4.78 (d, J=14.4 Hz, 1H), 3.87 (t, J=9.2 Hz, 1H), 2.89 (d, J=9.6 Hz, 1H), 2.85-2.79 (m, 1H), 2.68-2.60 (m, 2.50-2.19 (m, 4H), 2.0 (d, J=14.4 Hz, 1H), 1.71-1.64 (m, 1H), 1.55 (s, 3H), 1.16 (t, J 10.8 Hz, 1H). $^{13}$C NMR (CDCl$_3$, 100 MHz) δ 169.3, 164.8, 162.3, 146.4, 138.2, 135.0, 132.4, 121.1, 120.2, 108.7, 103.8, 80.9, 63.3, 60.0, 54.9, 42.6, 36.5, 25.2, 24.1, 23.7, 18.0 ppm.

Example 8. (1aR,7aS,10aS,10bS,E)-1a-Methyl-8-methylene-5((4-propyl-1H-1,2,3-triazol-1-yl)methyl)-2,3,6,7,7a,8,10a,10b-octahydrooxireno[2',3':9,10]cyclodeca[1,2-b]furan-9(1aH)-one (JVM 4-16)

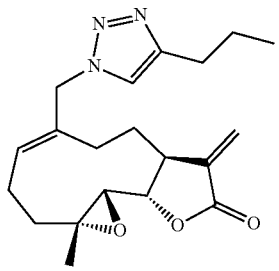 [SMILES: C=C1C(=O)O[C@H]2[C@H]1CC/C(Cn1cc(CCC)nn1)=C\CC[C@@]1(C)O[C@@H]21]

$^1$H NMR (CDCl$_3$, 400 MHz): δ 7.23 (s, 1H), 6.30 (d, J=3.6 Hz, 1H), 5.73 (t, J=8.0 Hz, 1H), 5.67 (d, J=3.2 Hz, 1H), 5.16 (d, J=14.4 Hz, 1H), 4.69 (d, J=14.8 Hz, 1H), 3.84 (t, J=9.2 Hz, 1H), 2.87 (d, J=9.2 Hz, 1H), 2.77-2.58 (m, 4H), 2.45-2.17 (m, 4H), 1.96 (d, J=15.2 Hz, 1H), 1.74-1.60 (m, 3H), 1.54 (s, 3H), 1.14 (t, J=11.2 Hz, 1H), 0.96 (t, J=6.8 Hz, 3H), $^{13}$C NMR (CDCl$_3$, 100 MHz) δ 169.3, 149.0, 138.3, 135.5, 131.9, 121.2, 120.2, 80.9, 63.5, 59.9, 54.8, 42.7, 36.7, 27.8, 25.3, 24.1, 23.8, 22.7, 18.0, 13.9 ppm.

Example 9. (1aR,7aS,10aS,10bS,E)-5((4-(3-Chlorophenyl)-1H-1,2,3-triazol-1-yl)methyl)-1a-methyl-8-methylene-2,3,6,7,7a,8,10a,10b-octahydrooxireno[2',3':9,10]cyclodeca[1,2-b]furan-9(1aH)-one (JVM 4-25)

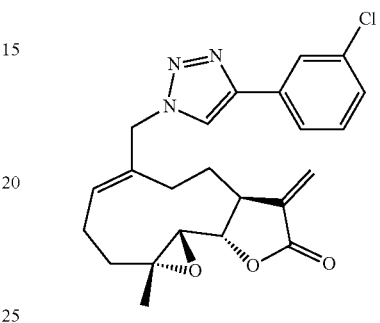

$^1$NMR (CDCl$_3$, 400 MHz): δ 7.81 (s, 1H), 7, 74 (d, J=7.6 Hz, 2H), 7.38-7.30 (m, 2H), 6.33 (d, J=3.2 Hz, 1H), 5.81 (t, J=8.0 Hz, 1H), 5.70 (d, J=3.2 Hz, 1H), 5.26 (d, J=14.8 Hz, 1H), 4.78 (d, J=14.4 Hz, 1H), 3.86 (t, J=9.6 Hz, 1H), 2.89-2.79 (m, 2H), 2.69-2.62 (m, 1H), 2.492.19 (m, 4H), 2.0 (d, J=14.4 Hz, 1H), 1.67 (t, J=12 Hz, 1H), 1.55 (s, 3H), 1.16 (t, J=11.6 Hz, 1H).

Example 10. (1aR,7aS,10aS,10bS,E)-5((4-(4-Fluorophenyl)-1H-1,2,3-triazol-1-yl)methyl)-1a-methyl-8-methylene-2,3,6,7,7a,8,10a,10b-octahydrooxireno[2',3':9,101cyclodeca[1,2-b]furan-9(1aH)-one (JVM 4-26)

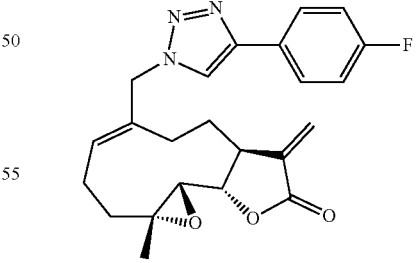

$^1$H NMR (CDCl$_3$, 400 MHz): δ 7.82-7.78 (m, 2H), 7.69 (s, 1H), 7.12 (t, J=8.8 Hz, 2H), 6.32 (d, J=2.80 Hz, 1H), 5.80 (t, J=8.4 Hz, 1H), 5.69 (d, J=3.2 Hz, 1H), 5.25 (d, J=14.4 Hz, 1H), 4.77 (d, J=14.4 Hz, 1H), 3.86 (t, J=9.6 Hz, 1H), 2.89-2.79 (m, 2H), 2.69-2.63 (m, 1H), 2.492.18 (n, 4H), 2.01 (d, J=15.6 Hz, 1H), 1.70-1.63 (m, 1H), 1.54 (s, 3H), 1.16 (t, J=11.6 Hz, 1H).

Example 11. (1aR,7aS,10aS,10bS,E)-5-((4-(4-Methoxyphenyl)-1H-1,2,3-triazol-1-yl)methyl)-1a-methyl-8-methylene-2,3,6,7,7a,8,10a,10b-octahydrooxireno[2',3':9,10]cyclodeca[1,2-b]furan-9(1aH)-one (JVM 4-24)

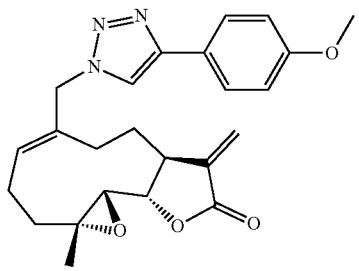 [SMILES: C=C1C(=O)O[C@H]2[C@H]1CC/C(Cn1cc(-c3ccc(OC)cc3)nn1)=C\CC[C@@]1(C)O[C@@H]21]

$^1$NMR (CDCl$_3$, 400 MHz): δ 7.76 (d, J=8.8 Hz, 1H), 7.63 (s, 1H), 6.97 (d, J=8.8 Hz, 1H), 6.32 (d, J=3.2 Hz, 1H), 5.79 (t, J=8.0 Hz, 1H), 5.69 (d, J=2.8 Hz, 1H), 5.24 (d, J=14.8 Hz, 1H), 4.75 (d, J=14 Hz, 1H), 3.88-3.84 (m, 4H), 2.89-2.79 (m, 2H), 2.74-2.63 (m, 1H), 2.48-2.18 (m, 4H), 2.01 (d, J=15.6 Hz, 1H), 1.65 (t, J=12.4 Hz, 1H), 1.54 (s, 3H), 1.15 (t, J=14.4 Hz, 1H).

Example 12. (1aR,7aS,10aS,10bS,E)-1a-Methyl-8-methylene-5-((4-phenyl-1H-1,2,3-triazol-1-yl)methyl)-2,3,6,7,7a,8,10a,10b-octahydrooxireno[2',3':9,10]cyclodeca[1,2-b]furan-9(1aH)-one (JVM 3-74)

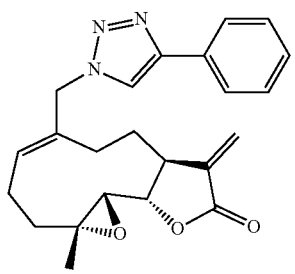 [SMILES: C=C1C(=O)O[C@H]2[C@H]1CC/C(Cn1cc(-c3ccccc3)nn1)=C\CC[C@@]1(C)O[C@@H]21]

$^1$H NMR (CDCl$_3$, 400 MHz): δ 7.84 (d, J=8 Hz, 2H), 7.73 (s, 1H), 7.43 (t, J=7.2 Hz, 2H), 7.34 (t, J=7.2 Hz, 1H), 6.32 (d, I=3.2 Hz, 1H), 5.80 (t, J=8.8 Hz, 1H), 5.70 (d, J=3.2 Hz, 1H), 5.26 (d, J=14.4 Hz, 1H), 4.78 (d, J=14.8 Hz, 1H), 3.86 (t, J=9.2 Hz, 1H), 2.89-2.79 (m, 2H), 2.72-2.62 (m, 1H), 2.48-2.17 (m, 4H), 2.01 (d, J=15.6 Hz, 1H), 1.70-1.62 (m, 1H), 1.54 (s, 3H), 1.16 (t, J=11.2 Hz, 1H). $^{13}$C NMR (CDCl$_3$, 100 MHz) δ 169.2, 148.5, 138.3, 135.3, 132.3, 130.4, 129.0, 128.5, 125.8, 121.7, 119.1, 80.9, 63.5, 59.9, 55.0, 42.7, 36.6, 25.3, 24.2, 23.6, 18.0 ppm.

Example 13. (1aR,7aS,10aS,10bS,E)-5-((4-(4-Fluoro-3-methylphenyl)-1H-1,2,3-triazol-1-yl)methyl)-1a-methyl-8-methylene-2,3,6,7,7a,8,10a,10b-octahydrooxireno[2',3':9,10]cyclodeca[1,2-b]furan-9(1aH)-one (JVM 4-27)

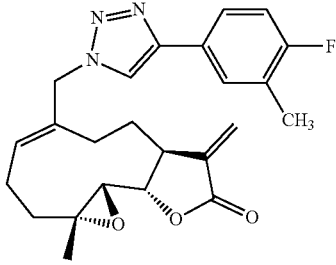 [SMILES: C=C1C(=O)O[C@H]2[C@H]1CC/C(Cn1cc(-c3ccc(F)c(C)c3)nn1)=C\CC[C@@]1(C)O[C@@H]21]

$^1$H NMR (CDCl$_3$, 400 MHz): δ 7.69 (d, J=8.4 Hz, 1H), 7.58 (t, J=5.2 Hz, 1H), 7.05 (t, J=8.8 Hz, 1H), 6.3 (d, J=3.2 Hz, 1H), 5.79 (t, J=8.4 Hz, 1H), 5.69 (d, J=2.8 Hz, 1H), 5.25 (d, J 14.4 Hz, 1H), 4.76 (d, J=14.4 Hz, 1H), 3.86 (t, J=9.6 Hz, 1H), 2.89-2.78 (m, 2H), 2.73-2.69 (m, 1H), 2.48-2.18 (m, 8H), 2.01 (d, J=15.2 Hz, 1H), 1.70 (t, J=15.2 Hz, 1H), 1.54 (s, 3H), 1.16 (t, J=12.8 Hz, 1H).

Example 14. (1aR,7aS,10aS,10bS,E)-5-((4-(3-Ethynyl phenyl)-1H-1,2,3-triazol-1-yl)methyl)-1a-methyl-8-methylene-2,3,6,7,7a,8,10a,10b-octahydrooxireno[2',3':9,10]cyclodeca[1,2-b]furan-9(1aH)-one (JVM 4-41)

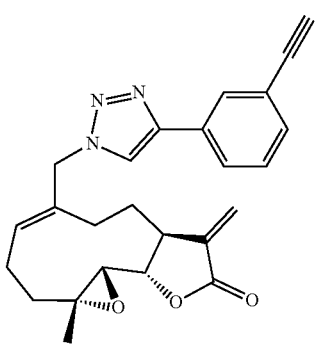 [SMILES: C#Cc1cccc(-c2cn(C/C3=C/CC[C@@]4(C)O[C@H]4[C@H]4OC(=O)C(=C)[C@@H]4CC3)nn2)c1]

$^1$H NMR (CDCl$_3$, 400 MHz): δ 7.91 (s, 1H), 7.88 (d, J=7.20 Hz, 1H), 7.75 (s, 1H), 7.47 (d, J=7.6 Hz, 1H), 7.40 (t, J=7.6 Hz, 1H), 6.32 (d, J=3.2 Hz, 1H), 5.80 (t, J=8 Hz, 1H), 5.70 (d, J=2.8 Hz, 1H), 5.26 (d, J=14.8 Hz, 1H), 4.77 (d, J=14.4 Hz, 1H), 3.86 (t, =9.6 Hz, 1H), 3.10 (s, 1H), 2.89-2.79 (m, 2H), 2.66-2.61 (m, 1H), 2.48-2.19 (m, 4H), 2.0 (d, J=15.6 Hz, 1H), 1.70-1.63 (m, 1H), 1.54 (s, 3H), 1.21-1.11 (m, 1H). $^{13}$C NMR (CDCl$_3$, 100 MHz) δ 169.2, 147.5, 138.2, 135.2, 132.4, 132.0, 130.7, 129.4, 129.1, 126.1, 122.8, 121.1, 119.5, 83.3, 80.9, 77.8, 63.4, 59.9, 55.0, 42.7, 36.6, 25.2, 24.2, 23.6, 18.0 ppm.

Example 15. (1aR,7aS,10aS,10bS,E)-1a-Methyl-8-methylene-5-((4-(pyridin-2-yl)-1H-1,2,3-triazol-1-yl)methyl)-2,3,6,7,7a,8,10a,10b-octahydrooxireno[2',3':9,10]cyclodeca[1,2-b]furan-9(1aH)-one (JVM 4-47)

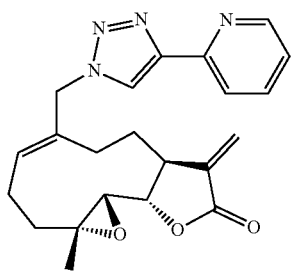 [SMILES: C=C1C(=O)O[C@H]2[C@H]1CC/C(Cn1cc(-c3ccccn3)nn1)=C\CC[C@@]1(C)O[C@@H]21]

$^1$H NMR (CDCl$_3$, 400 MHz): δ 7.8.57 (d, J=3.2 Hz, 1H), 8.19 (d, J=8 Hz, 1H), 8.12 (s, 1H), 7.80 (t, J=8 Hz, 1H), 7.26-7.23 (m, 1H), 6.32 (d, J=3.6 Hz, 1H), 5.83 (t, J=8.4 Hz, 1H), 5.69 (d, J=2.8 Hz, 1H), 5.26 (d, J=14.4 Hz, 1H), 4.79 (d, J=14.4 Hz, 1H), 3.86 (t, J=9.6 Hz, 1H), 2.89 (d, J=9.6 Hz, 1H), 2.84-2.78 (m, 1H), 2.68-2.59 (m, 1H), 2.47-2.18 (m, 4H), 2.01 (d, J=14.8 Hz, 1H), 1.70-1.63 (m, 1H), 1.54 (s, 3H), 1.15 (t, J=12.8 Hz, 1H). $^{13}$C NMR (CDCl$_3$, 100 M/hz) δ 169.2, 150.1, 149.5, 148.9, 138.3, 137.1, 134.8, 132.7, 123.1, 121.6, 121.0, 20.3, 80.9, 63.3, 59.9, 54.9, 42.6, 36.5, 25.2, 24.1, 23.5, 18.0 ppm.

REFERENCES FOR THE EXAMPLES

1. Knight, D. W. *Nat. Prod. Rep.* 1995, 12, 271.
2. (a) Skalska, J.; Brookes, P. S.; Nadtochiy, S. M.; Hilchey, S. P.; Jordan, C. T.; Guzman, M. Maggirwar, S. B.; Briehl, M. M.; Bernstein, S. H. *PLoS ONE* 2009, 4, e8115. (b) Shama, N.; Crooks. P. A. *Bioorg. Med. Chem. Lett.* 2008, 18, 3870. (d) Hewamana, S.; Alghazal, S.; Lin, T. T.; Clement, M.; Jenkins, C.; Guzman, M. L.; Jordan, C. T.; Neelakantan, S.; Crooks, P. A.; Burnett, A. K.; Pratt, G.; Fegan, C.; Rowntree, C.; Brennan, P.; Pepper, C. *Blood* 2008, 111, 4681. (e) Oka, D.; Nishimura, K.; Shiba, M.; Nakai, Y.; Arai, Y.; Nakayama, M.; Takayama, H.; Inoue, H.; Okuyama, A.; Nonomura, N. *Int. J. Cancer.* 2007, 120, 2576.
3. (a). Bork, P. M.; Schmitz, M. L.; Kuhnt, M.; Escher, C.; Heinrich, M. *FEBS Lett.* 1997, 402, 85. (b). Wen, J.; You, K. R.; Lee, S. Y.; Song, C. H.; Kim, D. G. *J. Biol. Chem.* 2002, 277, 38954. (c). Hehner, S. P.; Heinrich, M.; Bork, P. M.; Vogt, M.; Ratter, F.; Lehmann, V.; Schulze-Osthoff, K.; Droge, W.; Schmitz, M. L. *J. Biol. Chem.* 1998, 273, 1288. (d). Sweeney, C. J.; Li, L.; Shanmugam, R.; Bhat-Nakshatri, P. B.; Jayaprakasan, V.; Baldridge, L. A.; Gardner, T.; Smith, M.; Nakshatri, H.; Cheng, L. *Clin. Cancer Res.* 2004, 10, 5501. (e). Yip-Schneider, M. T.; Nakshatri, H.; Sweeney, C. J.; Marshall, M. S.; Wiebke, E. A.; Schmidt, C. M. *Mol. Cancer Ther.* 2005, 4, 587. (f) Nozaki, S.; Sledge, G. W.; Nakshatri, H. *Oncogene* 2001, 20, 2178. (g) Pei, S.; Minhajuddin, M.; Callahan, K. P.; Balys, L. Ashton, J. M.; Neering, S. J.; Lagadinou, E. D.; Corbett, C.; Ye, H.; Liesveld, J. L.; O'Dwyer, K. M.; Li, Z.; Shi, L.; Greninger, P.; Settleman, J.; Benes, C.; Hagen, F. K.; Munger, J.; Crooks, P. A.; Becker, M. W.; Jordan, C. T. *J. Biol. Chem.* 2013, 288, 33542.
4. (a) Guzman, M. L.; Rossi, R. M.; Karnischky, L.; Li, X.; Peterson, D. R.; Howard, D. S.; Jordan, C. T. *Blood* 2005, 105, 4163. (b) Guzman, M. L.; Jordan, C. T. *Expert Opin. Biol. Ther.* 2005, 5, 1147.
5. El-Feraly, F. S. *Phytochemistry* 1984, 23, 2372.
6. Macias, F. A.; Galindo, J. C. G.; Guillermo, M. M. *Phytochemistry* 1992, 31, 969.
7. Shama, N.; ShanShan P.; Fred, K. H.; Craig, T. J.; Peter, A. C. *Bioorg. Med. Chem.* 2011, 19, 1515.
8. Janganati, V.; Penthala, N. R.; Madadi, N. R.; Chen, Z.; Crooks, P. A. *Bioorg. Med. Chem. Lett.* 2014, 24, 3499.

What is claimed is:

1. A compound of Formula (II):

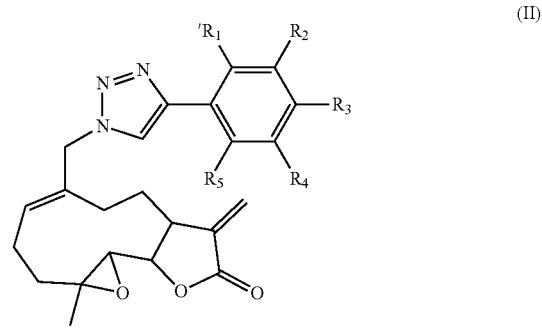

(II)

wherein:
$R_1$, $R_2$, $R_3$, $R_4$, and $R_5$ are each independently selected from the group consisting of hydrogen, hydrocarbyl, substituted hydrocarbyl, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heteroaryl, substituted heteroaryl, methyl, trifluoromethyl, halogen, cyano, nitro, amidine, amino, carboxyl, ester, alkylalkylamino, dialkylamino, hydroxyl, alkoxy or arylalkoxy (e.g. methoxy, ethoxy, benzyloxy, substituted benzyloxy) and combinations thereof; and $R_1$ and $R_2$ or $R_2$ and $R_3$ or $R_3$ and $R_4$ or $R_4$ and $R_5$ together can optionally form an optionally substituted cycloalkyl, aryl or heteroaryl 5 or 6 membered ring.

2. The compound of claim 1, wherein $R_1$, $R_2$, $R_3$, $R_4$, and $R_5$ are each independently selected from the group consisting of hydrogen, alkyl, substituted alkyl, alkynyl, methyl, trifluoromethyl, halogen, cyano, nitro, amidine, amino, carboxyl, ester, alkylalkylamino, dialkylamino, hydroxyl, alkoxy or arylalkoxy (e.g. methoxy, ethoxy, benzyloxy, substituted benzyloxy) and combinations thereof.

3. The compound of claim 1, wherein $R_1$, $R_2$, $R_3$, $R_4$, and $R_5$ are each independently selected from the group consisting of hydrogen, alkynyl, methyl, trifluoromethyl, halogen, amino, carboxyl, ester, hydroxyl, alkoxy (e.g. methoxy, ethoxy) and combinations thereof.

4. The compound of claim 1, wherein the compound is a fumarate salt.

5. A pharmaceutical composition comprising a compound of claim 1.

* * * * *